(12) United States Patent
Wolleschensky et al.

(10) Patent No.: US 7,274,446 B2
(45) Date of Patent: Sep. 25, 2007

(54) METHOD AND ARRANGEMENT FOR THE DEEP RESOLVED OPTICAL RECORDING OF A SAMPLE

(75) Inventors: Ralf Wolleschensky, Schoeten (DE); Michael Kempe, Kunitz (DE)

(73) Assignee: Carl Zeiss Jena GmbH, Jena (DE)

( * ) Notice: Subject to any disclaimer, the term of this patent is extended or adjusted under 35 U.S.C. 154(b) by 1130 days.

(21) Appl. No.: 10/043,009

(22) Filed: Jan. 8, 2002

(65) Prior Publication Data

US 2003/0132394 A1 Jul. 17, 2003

Related U.S. Application Data

(60) Provisional application No. 60/288,249, filed on May 2, 2001.

(30) Foreign Application Priority Data

Apr. 7, 2001 (DE) ................. 101 18 463
Nov. 8, 2001 (DE) ................. 101 55 002

(51) Int. Cl.
  *G01J 3/02* (2006.01)
  *G01N 21/64* (2006.01)
(52) U.S. Cl. .............. 356/300; 356/317; 250/458.1
(58) Field of Classification Search ............. 356/300, 356/317, 326, 328, 610
  See application file for complete search history.

(56) References Cited

U.S. PATENT DOCUMENTS

| 4,929,951 A | 5/1990 | Small |
| 5,003,187 A | 3/1991 | Zumbrunn et al. |
| 5,381,236 A | 1/1995 | Morgan |
| 5,867,604 A | 2/1999 | Ben-Levy et al. |

FOREIGN PATENT DOCUMENTS

| DE | 199 30 816 | 7/1999 |
| WO | 98/45745 | 10/1998 |
| WO | 98/52021 | 11/1998 |

OTHER PUBLICATIONS

Cole et al, Time-domain whole-field fluorescence lifetime imaging with optical sectioning, Journal of Microscopy, vol. 203, Pt 3, Sep. 2001, pp. 246-257.*

Gruber et al. Simple, Robust and Accurate Phase-Measuring Triangulation Optik, Wissenschaftliche Verlag Gmbh, Stuggart, DE, vol. 89, No. 3, pp. 118-122, Jan. 1992.

* cited by examiner

*Primary Examiner*—F. L. Evans
(74) *Attorney, Agent, or Firm*—Reed Smith LLP

(57) ABSTRACT

A method for depth-resolved optical detection of a specimen comprises the steps of providing a scanning movement over the specimen or at least a part of the specimen of an illumination light distribution of at least one wavelength which is generated on or in the specimen, providing detection particularly of the light which is influenced based on interaction with the specimen, especially fluorescent light and/or reflected light and/or luminescent light and/or scattered and/or transmitted light, the illumination light having a modulation in at least one spatial direction, and carrying out the scanning movement and detection associated with the scanning with the scanning movement at least in a first and a second different phase position of the modulation and/or first and second frequency of the periodicity of the modulation and calculating at least one optical section image through the specimen or through part of the specimen. Other methods and arrangements are disclosed.

92 Claims, 26 Drawing Sheets

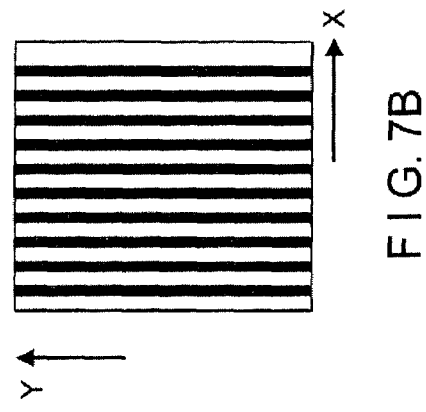
FIG. 7B
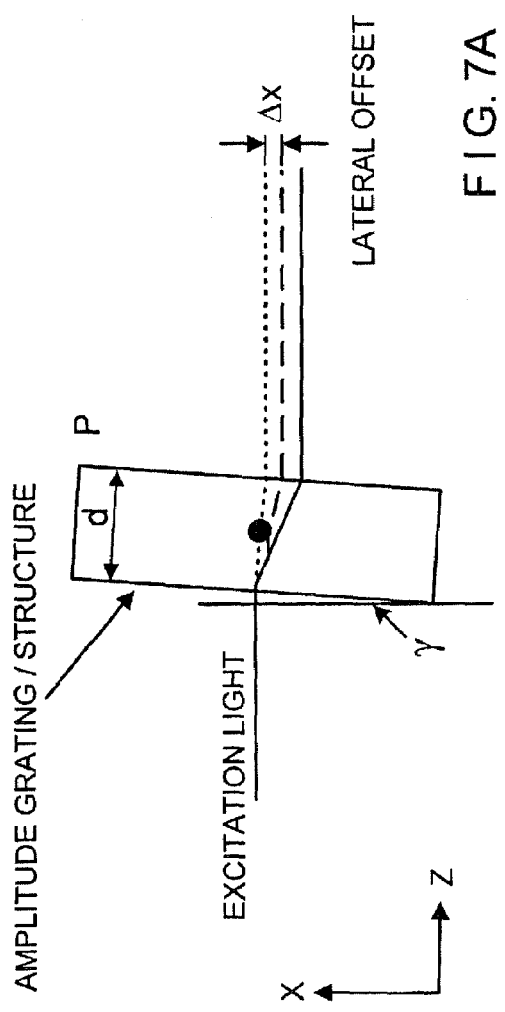
FIG. 7A
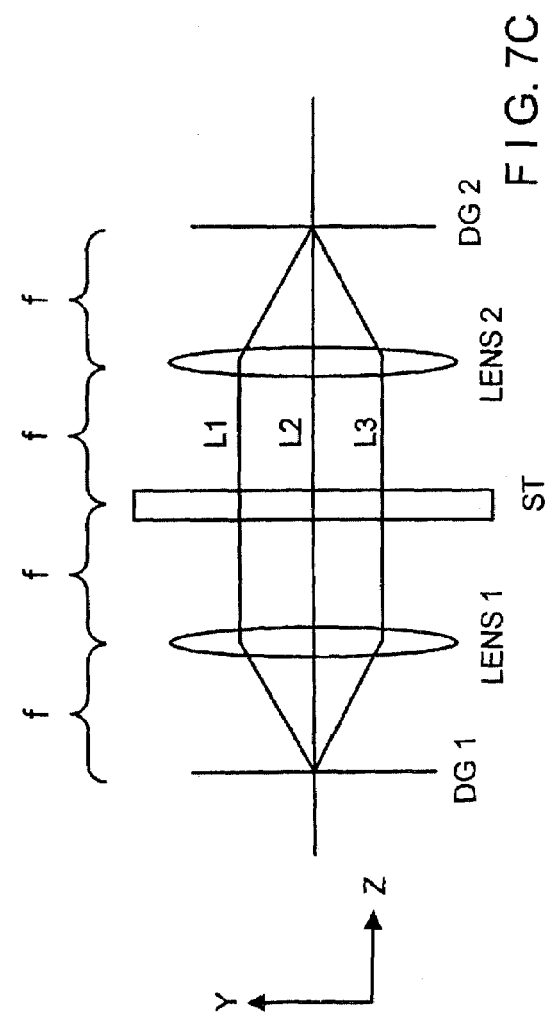
FIG. 7D
FIG. 7C

DIFFERENT ARRANGEMENTS FOR LIGHT SOURCE MODULE

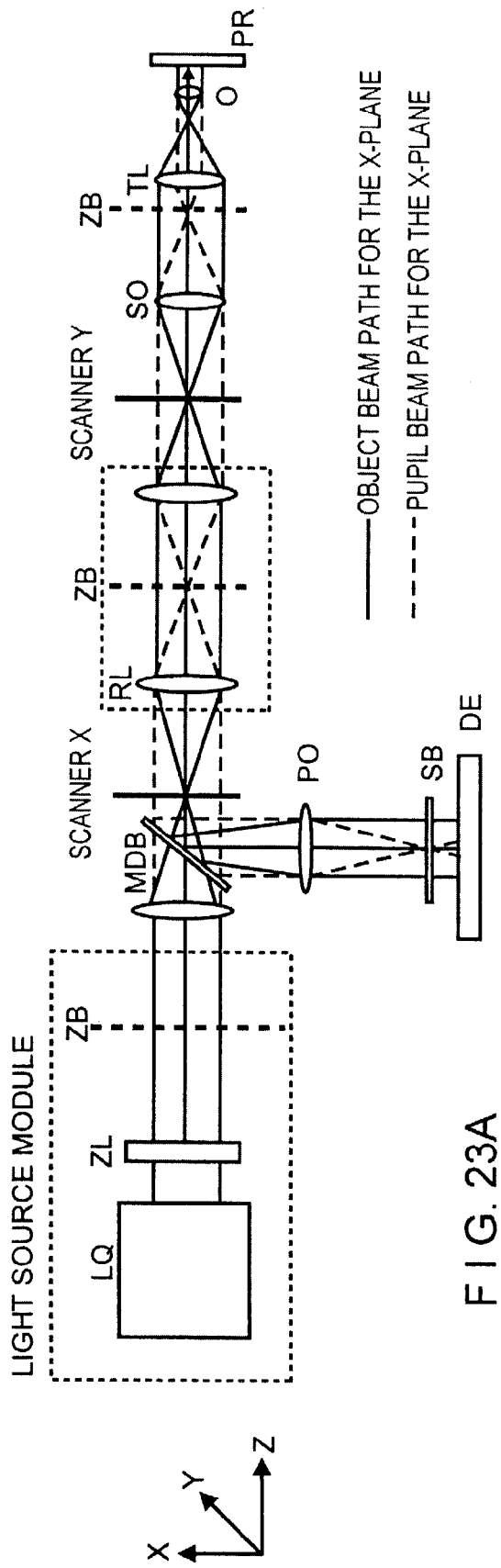
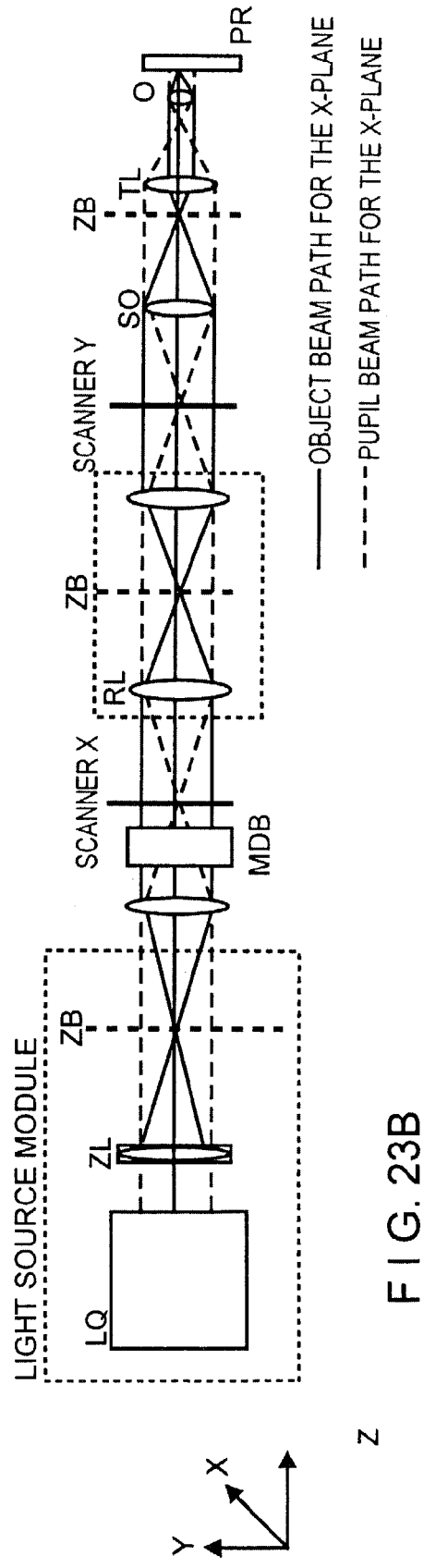
FIG. 23A
FIG. 23B

METHOD AND ARRANGEMENT FOR THE DEEP RESOLVED OPTICAL RECORDING OF A SAMPLE

CROSS REFERENCE TO RELATED APPLICATIONS

This application claims priority of provisional application Ser. No. 60/288,249, filed May 2, 2001 and German Application No. 101 18 463.8, filed Apr. 7, 2001 and German Application No. 101 55 002.2, filed Nov. 8, 2001, complete disclosures of which are hereby incorporated by reference.

BACKGROUND OF THE INVENTION a) Field of the Invention

The invention is directed to a method and an arrangement in microscopy, particularly fluorescence laser scanning microscopy, for examination of predominantly biological specimens, preparations and associated components. This includes methods for screening active ingredients based on fluorescence detection (high throughput screening) and methods of laser scanning microscopy based upon other contrast mechanisms.

b) Description of the Related Art

A typical area of application of light microscopy for examining biological preparations is fluorescence microscopy (Pawley, "Handbook of Biological Confocal Microscopy"; Plenum Press 1995). In this case, determined. dyes are used for specific labeling of cell parts.

The irradiated photons having a determined energy excite the dye molecules from the ground state to an excited state by the absorption of a photon. This excitation is usually referred to as single-photon absorption (FIG. 1a). The dye molecules excited in this way can return to the ground state in various ways, In fluorescence microscopy, the most important is the transition with emission of a fluorescence photon, Because of the Stokes shift, there is generally a red shin in the wavelength of the emitted photon in comparison to the excitation radiation; that is, it has a greater wavelength. Stokes shift makes it possible to separate the fluorescence radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, several parts of a preparation can also be dyed simultaneously with different dyes which bind in a specific manner (multiple fluorescence). Special dichroic beam splitters are used again to distinguish between the fluorescence signals emitted by the individual dyes.

In addition to excitation of dye molecules with a high-energy photon (single-photon absorption), excitation with a plurality of low-energy photons is also possible (FIG. 1b). The sum of energies of the single photons corresponds approximately to that of the high-energy photon. This type of excitation of dyes is known as multiphoton absorption (Corle, Kino, "Confocal Scanning, Optical Microscopy and Related Imaging Systems", Academic Press 1996). FIG. 1b shows excitation by means of simultaneous absorption of two photons in the near infrared wavelength region. However, the dye emission is not influenced by this type of excitation, i.e., the emission spectrum undergoes a negative Stokes shift in multiphoton absorption; that is, it has a smaller wavelength compared to the excitation radiation. The separation of the excitation radiation from the emission radiation is carried out in the same way as in single-photon excitation.

The prior art will be explained more fully in the following by way of example with reference to a confocal laser scanning microscope (LSM) (FIG. 2).

An LSM is essentially composed of four modules: light source L, scan module S, detection unit DE and microscope M, These modules are described more fully in the following. In addition, reference is had to DE19702753A1 and U.S. Pat. No. 6,167,173.

Lasers with different wavelengths are used in an LSM for specific excitation of different dyes in a preparation. The choice of the excitation wavelength is governed by the absorption characteristics of the dyes to be examined. The excitation radiation is generated in the light source module L. Various lasers A–D (argon, argon/krypton, Ti:Sa lasers) are used for this purpose. Further, the selection of wavelengths and the adjustment of the intensity of the required excitation wavelength is carried out in the light source module L, e.g., using an acousto-optic modulator. The laser radiation subsequently reaches the scan module S via a fiber or a suitable mirror arrangement. The laser radiation generated in the light source L is focused in the preparation (specimen 3) in a diffraction-limited manner by the objective (2) via the scanner, scan lens and tube lens. The focus is moved over the specimen 3 two-dimensionally in x-y direction. The pixel dwell times when scanning over the specimen 3 are mostly in the range of less than one microsecond to several seconds.

In confocal detection (descanned detection) of fluorescent light, the light emitted from the focal plane (specimen 3) and from the planes located above and below the latter reaches a dichroic beam splitter (MDB) via the scanner. This dichroic bean) splitter separates the fluorescent light from the excitation light. The fluorescent light is subsequently focused, via dichroic beam splitters DBS 1–3 and pinhole optics, on a diaphragm (confocal diaphragm/pinhole) (PH1, 2, 3, 4) located precisely in a plane conjugate to the focal plane of the objective 2. In this way, fluorescent light components outside of the focus are suppressed. The optical resolution of the microscope can be adjusted by varying the size of the diaphragm. Another dichroic blocking filter (EF1-4) which again suppresses the excitation radiation is located behind the diaphragm. After passing the blocking filter, the fluorescent light is measured by means of a point detector (PMT1-4).

When using multiphoton absorption, the excitation of the dye fluorescence is carried out in a small volume in which the excitation intensity is particularly high. This area is only negligibly larger than the detected area when using a confocal arrangement. Accordingly, a confocal diaphragm can be dispensed with and detection can be carried out directly after the objective, with reference to the detection direction, or on the side remote of the objective (non-descanned detection) via T-PMT, PMT 5.

In another arrangement (not shown) for detecting a dye fluorescence excited by multiphoton absorption, descanned detection is earned out again, but this time the pupil of the objective is imaged by the pinhole optics PH in the detection unit (non-confocal descanned detection).

From a three-dimensionally illuminated image, only the plane (optical section or slice) coinciding with the focal plane of the objective is reproduced by the above-described detection arrangements in connection with corresponding single-photon absorption or multiphoton absorption. By recording a plurality of optical slices in the x-y plane at different depths z of the specimen, a three-dimensional image of the specimen can be generated subsequently in computer-assisted manner.

Accordingly, the LSM is suitable for examination of thick preparations. The excitation wavelengths are determined by the utilized dye with its specific absorption characteristics. Dichroic filters adapted to the emission characteristics of the dye ensure that only the fluorescent light emitted by the respective dye will be measured by the point detector.

According to the prior art, line scanners, as they are called, are also used instead of point scanners (Corle, Kino, "Confocal Scanning Optical Microscopy and Related Imaging Systems", Academic Press 1996). The basic construction essentially corresponds to that of an LSM according to FIG. 2. However, instead of a point focus, a line is imaged in the specimen (3) and the specimen to be examined is scanned in only one direction (x or y). The line focus is generated by means of at least one cylindrical lens ZL (shown in dashes in FIG. 2) in the collimated illumination beam path, a pupil plane of the microscope arrangement being located in the focal length of the latter. In a construction of this kind, a slit diaphragm instead of a pinhole diaphragm PH 1–4 is used as confocal diaphragm (PH). Non-descanned detection can also be carried out with this arrangement when using multiphoton absorption. In this connection, the confocal diaphragm (PH) can be omitted again. A CCD camera (non-descanned) or line (descanned) with 1024 or more image points can be used for detection instead of the point detector (PMT). The image acquisition rate can be substantially increased by scanning a line instead of a point. Therefore, this scanning method can be used for observing high-speed processes in real time (real time microscopy).

It is disadvantageous in this method that the depth resolution through the slit diaphragm is reduced by a factor of 1.4 compared with point-scanning laser scanning microscopes, This is due to the fact that the confocal slit diaphragm suppresses only fluorescent light components outside of the confocal section at right angles to the scan line. Lateral resolution is also worse.

In another arrangement for real time microscopy according to the prior art, the entire field to be examined is illuminated by an expanded light source. However, only special point patterns of the total field to be scanned are uncovered by a rapidly rotating disk. These methods are mostly known in technical literature as Nipkow disk methods (Code, Kino, "Confocal Scanning, Optical Microscopy and Related Imaging Systems", Academic Press 1996).

In another method according to the prior art, known as structured illumination (see FIG. 3), the modulation depth of the optical imaging of an amplitude structure (e.g., grating) is used as a criterion for depth of field. The image of the periodic structure is distinguished by the frequency of the modulation and the phase position (image phase) of the modulation.

Various projection scenarios can be obtained by means of a phase shift of the structure at right angles to the optical axis.

Generally, at least three phase images PB are required at 0°, 120° and 240° in order to calculate depth-discriminated optical sections without stripes. These phase images (PB) are subsequently calculated to form a (confocal) optical section image in an image processor by the following formula:

where I(x, angle) describes the intensity at the respective pixel in the corresponding phase image.

It is simplest to carry our the recording of three or more phase images sequentially. In this connection, it is assumed that the specimen is not moved during the measurement of the images. The section images or section slacks which are calculated from the phase images in this way can be displayed subsequently on a standard PC and monitor by means of 3-D evaluating software. The spatial resolution along the optical axis depends on the wavelength of the light, the numeric aperture of the objective and the modulation frequency. For a detailed description of the calculation algorithm, reference is had to T. Wilson, et al., "Method of obtaining sectioning by using structured light in a conventional microscope", Optics Letters 22 (24), 1997.

A further disadvantage in previous methods for real time microscopy consists in that multiple detection devices must be provided when a plurality of dyes are examined simultaneously. This heightens the requirements for data transfer and increases the cost of a device of this kind. Therefore, at present, only microscopes are used for sequential image display of different dye fluorescences. DE 19829981 A1 describes a method for changing the excitation wavelengths and/or the intensity during the scanning process.

OBJECT AND SUMMARY OF THE INVENTION

It is the primary object of the invention to provide a novel method by which the preparations can be imaged in real time and with high optical resolution.

This object is met by a method for depth-resolved optical detection of a specimen comprises the steps of providing a scanning movement over the specimen or at least a part of the specimen of an illumination light distribution of at least one wavelength which is generated on or in the specimen, providing detection particularly of the light which is influenced based on interaction with the specimen, especially fluorescent light and/or reflected light and/or luminescent light and/or scattered and/or transmitted light, the illumination light having a modulation in at least one spatial direction, and carrying out the scanning movement and detection associated with the scanning with the scanning movement at least in a first and a second different phase position of the modulation and/or first and second frequency of the periodicity of the modulation and calculating at least one optical section image through the specimen or through part of the specimen.

Further in accordance with the invention, an arrangement for depth-resolved optical detection of a specimen, especially of the light of an illumination light distribution which is influenced based on interaction with the specimen, especially fluorescent light and/or reflected light and/or luminescent light and/or scattered and/or transmitted light comprising means for illuminating the specimen with at least one wavelength, means for generating a relative movement between the specimen and illumination light, means for imaging the light influenced by the specimen on at least one detector, means for imaging a structure which changes in a spatially periodic manner in at least one dimension in $$I_{Section}(x) = Const \cdot \sqrt{(I(x, 0°) - I(x, 120°))^2 + (I(x, 120°) - I(x, 240°))^2 + (I(x, 0°) - I(x, 240°))^2},$$

different phrases and/or frequencies of the periodicity on the specimen and means for calculating at least one optical section image from the local information of the light influenced by the specimen.

The invention is particularly suited for use in applications requiring multiple fluorescences, since these can be recorded simultaneously and advantageously also with optical resolution comparable to a point-scanning LSM, but in real time.

The method can be used in image-displaying microscope systems such as laser scanning microscopes for three-dimensional examination of biological preparations with an optical, spatial resolution of up to 200 nm and in analytic microscope systems such as fluorescence correlation spectrometers.

Further, fluorescence detection-based methods for screening dyes such as in chip readers are included. These methods differ from the methods of laser scanning microscopy primarily in that the image field is appreciably larger.

BRIEF DESCRIPTION OF THE DRAWINGS

In the drawings:

FIGS. 7A–D schematically show phase coding realized in a possible arrangement;

FIGS. 23A and B schematically show laser scanning microscopes with arrangements for the interference of partial light beams which contain a light module.

BRIEF DESCRIPTION OF THE INVENTION
AND THE PREFERRED EMBODIMENTS

Figure 4:
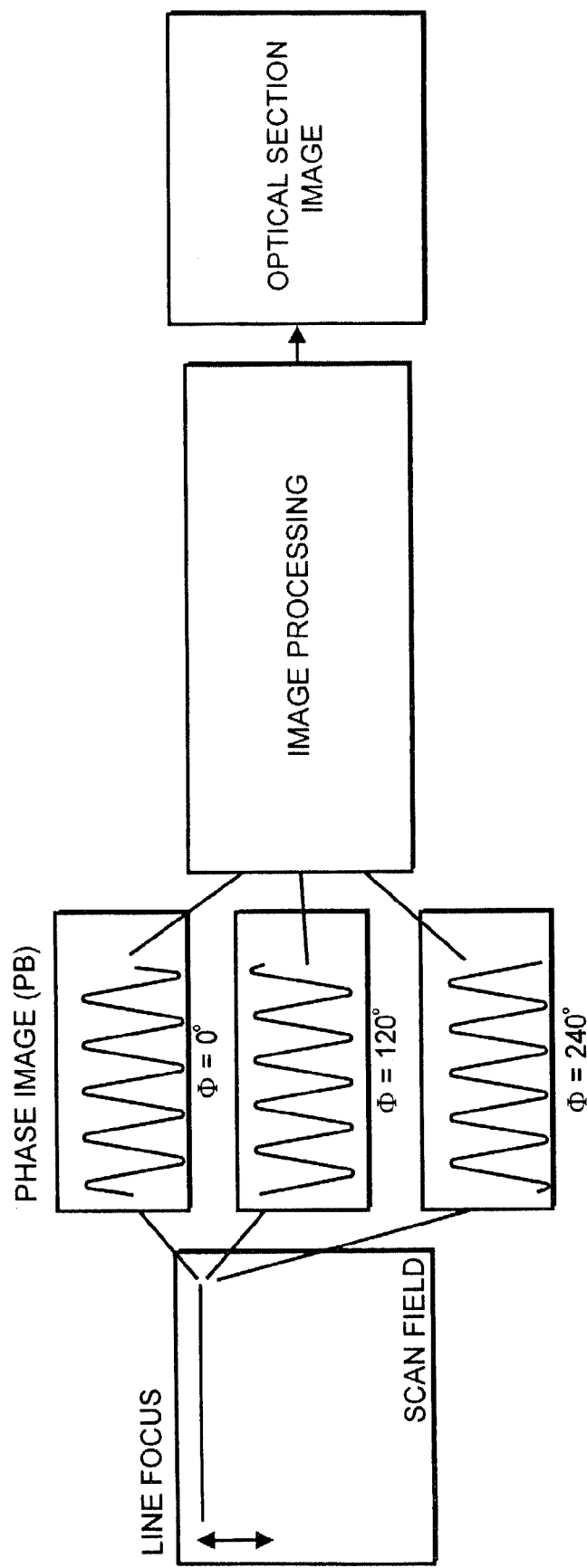
FIG. 4 shows a possible method flow chart.

The object of the method for increasing spatial detection resolution, preferably in a method displaying images in real time, is a line-shaped excitation and detection of the excitation radiation and/or excited fluorescence reflected, scattered and/or transmitted by a specimen. For this purpose, a line focus of the excitation radiation is generated in the specimen by means of suitable optics which are described more fully in the following. FIG. 4 shows a possible measurement flow chart. A scan field with the line focus is shown on the left-hand side. The line focus can be displaced along the arrow by suitable auxiliary means (scanner mirror in one direction). The increase in axial and lateral resolution is carried out by means of a structuring of the line focus. The structuring is carried out by superposing the scan line with a periodic structure which is generated, for example, by a sine grating in the beam path. With coherent illumination, a structure can also be generated in the specimen by means of the interference of two coherent partial beams (Wilson, WO98/45745). At least two images with different phase positions of the periodic structure are recorded. In principle, the optical section can also be carried out by recording images with different modulation frequencies of the structure.

The illumination of the specimen can be carried out with spatially and temporally coherent or incoherent illumination. For example, a spatially coherent laser light source can also be used by employing a diffusion screen or by arraying a plurality of individual foci in the specimen for an incoherent illumination.

At least two phase images PB with image phases of, e.g., 0° and 180° are advantageously required when using an excitation wavelength for calculating an optical section image in the image processor. With n excitation wavelengths, n+1 phase images are necessary. For one excitation wavelength, the signal emitted by the specimen has the following form along a scan line:

$$I_{Sig}(x) = C(x) \cdot \cos(k \cdot x) + B(x),$$

where $C(x)$ contains the actual object information (e.g., the concentration and effective cross section of the dye or the local reflection coefficient) at position x inside the confocal optical section and along the line focus for the excitation wavelength and represents the sought for quantity. $B(x)$ contains the object information outside of the confocal area. B(x) is not modulated, since the structure is not focused sharply outside the confocal area, The inverse modulation frequency of the structured excitation is represented by k. The above equation has two unknowns C(x) and B(x), To determine C(x), it is necessary to take two phase images. Let the phase images be designated by $I_i(x)$, i=0, 1, . . . n and characterized by a relative phase displacement of the modulation of i·Δφ (image phases), where the following equation system results:

$$I_0(x)=C(x)\cdot\cos(k\cdot x)+B(x)$$

$$I_1(x)=C(x)\cdot\cos(k\cdot x+\Delta\phi)+B(x)$$

The sought for object information is given by solving the equation system for C as follows:

$$C(x) = \frac{I_1(x) - I_0(x)}{\cos(k\cdot x\cdot\Delta\varphi) - \cos(k\cdot x)}.$$

To determine C(x), two images with different modulation frequencies $k_0$ and $k_1$ can also be taken in an analogous manner. Let the frequency images be designated by $I_i(x)$, i=0, 1, . . . n, so that the following equation system results:

$$I_0(x)=C(x)\cdot\cos(k_0\cdot x)+B(x)$$

$$I_1(x)=C(x)\cdot\cos(k_1\cdot x)+B(x)$$

The sought for object information is given by solving the equation system for C as follows:

$$C(x) = \frac{I_1(x) - I_0(x)}{\cos(k_1\cdot x) - \cos(k_0\cdot x)}.$$

C(x) can also be obtained by taking at least two images with different phases and frequencies of modulation.

An optical section in at least one specimen plane is composed of this line-related object information and can be further processed according to the prior art to obtain at least one image of at least one image stack.

When only one excitation wavelength is used and at least three phase images (e.g., with relative phase positions of 0°, 120° and 240°) are recorded, the algorithm for obtaining the object information explained according to the prior art (T. Wilson, et al., "Method of obtaining sectioning by using structured light in a conventional microscope", Optics Letters 22 (24), 1997) can also be applied in all of the arrangements described herein.

When a plurality of wavelengths are excited simultaneously, the subsequent separation of the signals of the specimen is canned out by a special phase coding or frequency coding of the modulation structure for the different excitation wavelengths. In general, the quantity of phase images required for n simultaneous excitation wavelengths is n+1. In this connection, different excitation wavelengths are separated from one another by a defined wavelength-specific position displacement of the modulation (coding phase) and/or a characteristic modulation frequency (coding frequency). The light emitted by the specimen (e.g., fluorescence) which occurs through an interaction with the excitation light of the respective wavelength with the specimen then possesses the specific coding phase and/or coding frequency depending on the excitation wavelength and can accordingly be separated according to the algorithm which will be given in the following.

Figure 5:
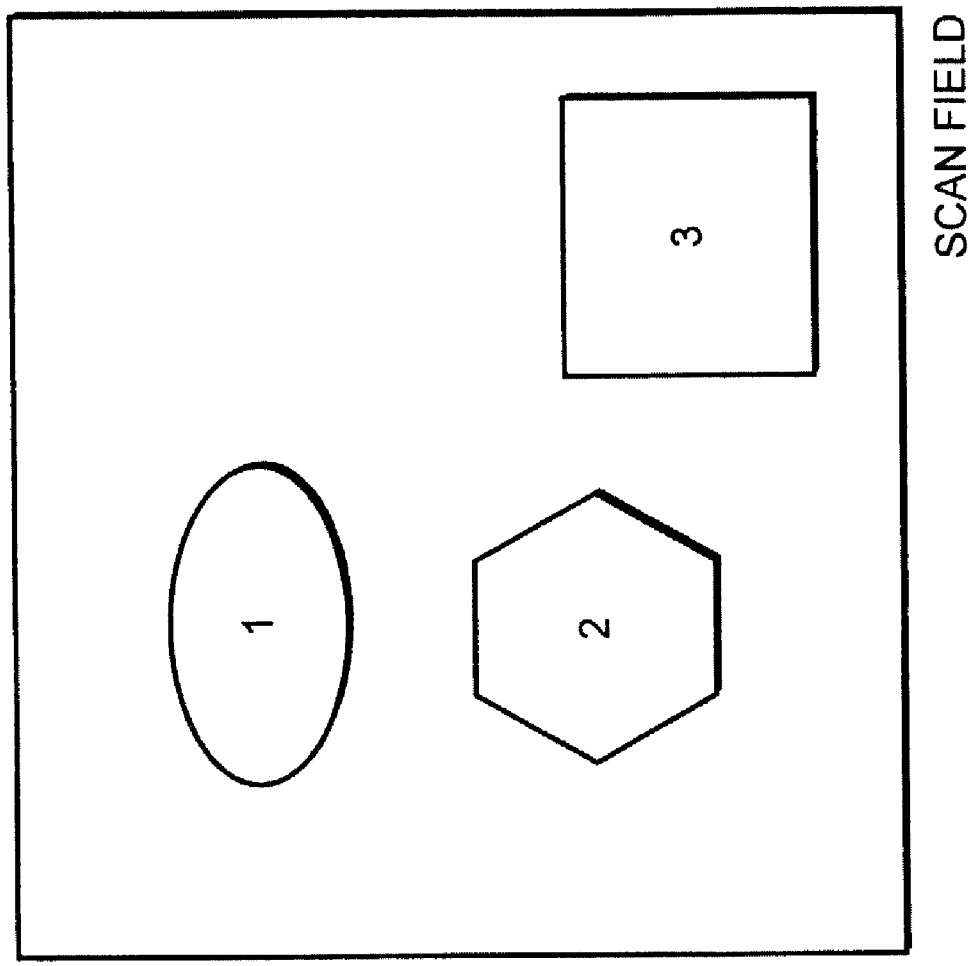
FIG. 5 schematically shows specimens dyed by different dyes in the scanning field which require different wavelengths to excite fluorescence.
Figure 6:
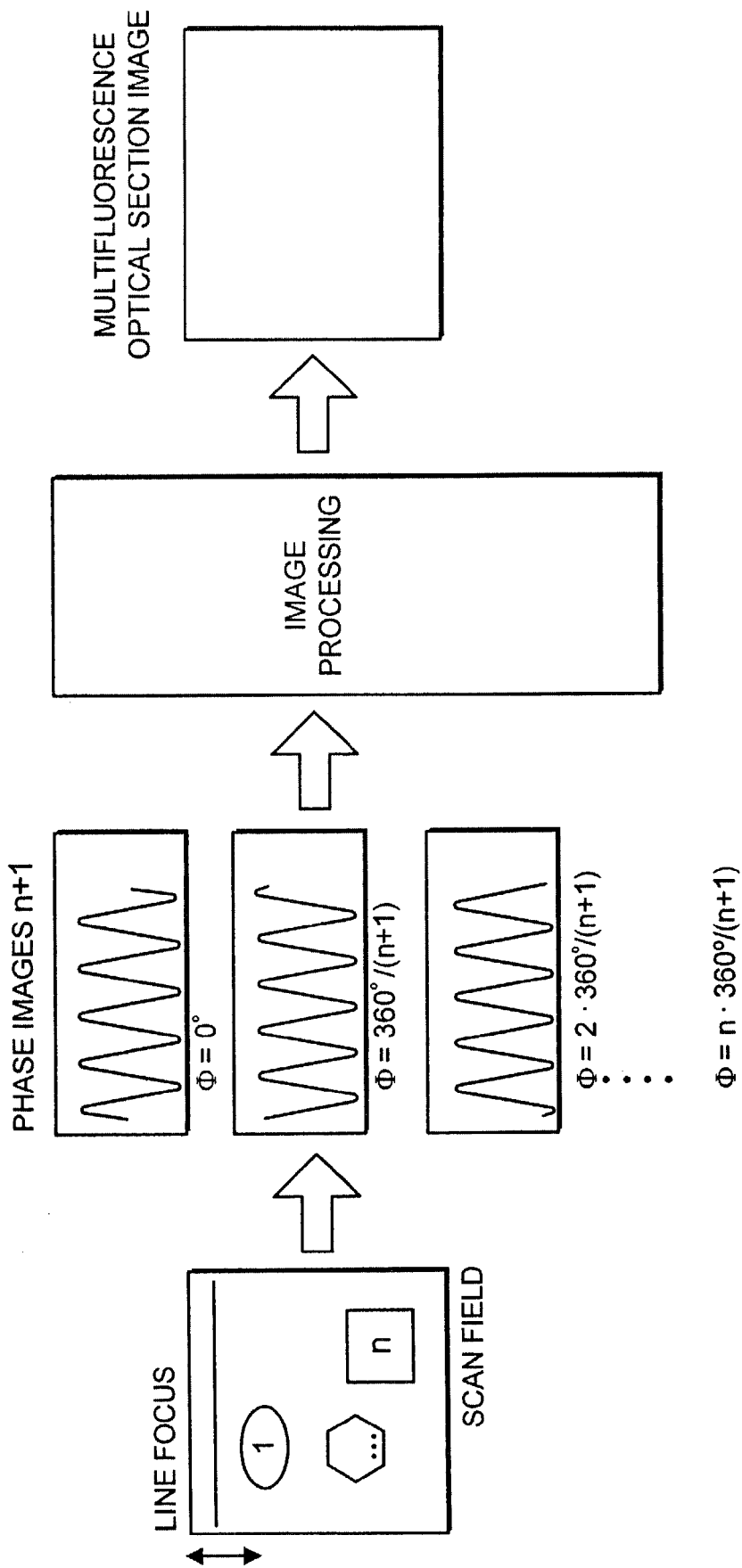
FIG. 6 illustrates schematically that with respect to FIG. 5, the coding frequency and/or the coding phrases of the excitation scan line transfer(s) to the detected fluorescence in the reoperative region.

Accordingly, when a specimen such as that shown in FIG. 5 is dyed by different dyes (1, 2, 3) in the scanning field which require different wavelengths ($L_1$, $L_2$, $L_3$) to excite fluorescence, the coding frequency ($f_1$, $f_2$, $f_3$) and/or the coding phases ($\phi_1$, $\phi_2$, $\phi_3$) of the excitation scan line transfers) to the detected fluorescence in the respective region (1, . . . n), see FIG. 6.

Preferably, all excitation wavelengths have the same coding frequency, i.e., one modulation frequency, but different coding phases. The following discussion is restricted to this case with phase coding, wherein a coding by means of modulation frequency is to be treated analogously and is the subject of the invention.

For two excitation wavelengths, the signal emitted by the specimen has the following form along a scan line:

$$I_{Sig}(x)=C_1(x)\cdot\cos(k\cdot x+\phi_1)+B_1(x)+C_2(x)\cdot\cos(k\cdot x+\phi_2)+B_2(x),$$

where $C_1(x)$ or $C_2(x)$ represents the sought for object information (e.g., the concentration and effective cross section of the dye) at position x inside the confocal optical section and along the line focus for the two excitation wavelengths. $B_1(x)$ or $B_2(x)$ contains the object information outside of the confocal area. $B_1(x)$ and $B_2(x)$ are not modulated, since the structure is not focused sharply outside the confocal area. $\phi_1$ and $\phi_2$ are the coding phases assigned to the respective excitation wavelengths, and k is the inverse modulation frequency (which is identical for both excitation wavelengths in this example) of the structured excitation. The above equation has four unknowns $C_1(x)$, $B_1(x)$, $C_2(x)$ and $B_2(x)$.

To determine $C_1(x)$ and $C_2(x)$, it is necessary to take three phase images. Let the phase images be designated by $I_i(x)$, i+0, 1, . . . n and characterized by a relative phase displacement of the modulation of i·Δφ (image phases), where the following equation system results:

$$I_0(x)=C_1(x)\cdot\cos(k\cdot x+\phi_1)+B_1(x)+C_2(x)\cdot\cos(k\cdot x+\phi_2)+B_2(x),$$

$$I_1(x)=C_1(x)\cdot\cos(k\cdot x+\phi_1\Delta\phi)+B_1(x)+C_2(x)\cdot\cos(k\cdot x+\phi_2+\Delta\phi)+B_2(x),$$

$$I_2(x)=C_1(x)\cdot\cos(k\cdot x+\phi_1+2\cdot\Delta\phi)+B_1(x)+C_2(x)\cdot\cos(k\cdot x+\phi_2+2\cdot\Delta\phi)+B_2(x),$$

The sought for object information is given by solving the equation system for $C_1$ and $C_2$ as follows:

$$C_1(x)=[-c_{12}(x)\cdot(I_2(x)-I_0(x))+c_{22}(x)\cdot(I_1(x)-I_0(x))]/\det(x)$$

$$C_2(x)=[c_{11}(x)\cdot(I_2(x)-I_0(x))+c_{21}(x)\cdot(I_1(x)-I_0(x))]/\det(x),$$

where $c_{ij}(x)=\cos(k\cdot x+\phi_j+i\cdot\Delta\phi)-\cos(k\cdot x+\phi_j)$ and $\det(x)=c_{11}(x)\cdot c_{22}(x)-c_{12}(x)\cdot c_{21}(x)$.

Thus, in order to obtain the object information, the coding phases ($\phi_j$) and the inverse modulation frequency (k) for the individual excitation wavelengths must be known. In order to solve the equation system and accordingly to separate the object information which was made visible by the respective excitation wavelength, three phase images are required in the case of two-dye excitation, wherein the image phase displacement (Δφ) between the individual images is 120° in the simplest case.

The object information from outside the confocal area can only be obtained for the sum of the amounts of all exciting wavelengths. In the present example, this background is:

$$B_1(x)+B_2(x)=I_0(x)-C_1(x)\cdot\cos(k\cdot x+\phi_1)-C_2(x)\cdot\cos(k\cdot x+\phi_2)$$

which can be calculated when $C_1$ and $C_2$ are known.

Expansion to three excitation wavelengths is given in equivalent manner from the solution of the corresponding equation system, where $C_3(x)$ or $B_3(x)$ represents the object information excited by the third wavelength from inside or outside the confocal section. The object information for the individual wavelengths is given as follows:

$$C_1=[(c_{12}\cdot c_{23}-c_{13}\cdot c_{22})\cdot(I_3-I_0)+(c_{13}\cdot c_{32}-c_{12}\cdot c_{33})\cdot(I_2-I_0)+(c_{22}\cdot c_{33}-c_{23}\cdot c_{32})\cdot(I_1-I_0)]/\det$$

$$C_2=[(c_{13}\cdot c_{21}-c_{11}\cdot c_{23})\cdot(I_3-I_0)+(c_{11}\cdot c_{33}-c_{13}\cdot c_{31})\cdot(I_2-I_0)+(c_{23}\cdot c_{31}-c_{21}\cdot c_{33})\cdot(I_1-I_0)]/\det$$

$$C_3=[(c_{11}\cdot c_{22}-c_{12}\cdot c_{21})\cdot(I_3-I_0)+(c_{12}\cdot c_{31}-c_{11}\cdot c_{32})\cdot(I_2-I_0)+(c_{21}\cdot c_{32}-c_{22}\cdot c_{31})\cdot(I_1-I_0)]/\det$$

with $\phi 3(x)$ as coding phase of the modulation in the third excitation wavelength and $\det(x)=c_{11}\cdot(c_{22}\cdot c_{33}-c_{23}\cdot c_{32})+c_{12}\cdot(c_{23}\cdot c_{31}-c_{21}\cdot c_{33})+c_{13}\cdot(c_{21}\cdot c_{32}-c_{22}\cdot c_{31})$.

With a three-dye excitation, four phase images are necessary for separating the object information, excited by the individual wavelengths. The image phase step size can be 90 degrees, for example. Since the values $c_{ij}$ are constant for an arrangement with predetermined coding phases and coding frequencies, obtaining the object information by signal processing is a simple operation. This operation can be indicated by the transformation of the scaled image signals $\Delta I_j(x)=I_j(x)-I_0(x)$ by means of factors $f_k(x)$ which are stored as constants and which are given by $c_{ij}(x)$. For three wavelengths, the equations above give, e.g., $$C_1 f_1 \cdot \Delta I_3 + f_2 \cdot \Delta I_2 + f_3 \cdot \Delta I_1$$

$$C_2 f_4 \cdot \Delta I_3 + f_5 \cdot \Delta I_2 + f_6 \cdot \Delta I_1$$

$$C_3 f_7 \cdot \Delta I_3 + f_8 \cdot \Delta I_2 + f_9 \cdot \Delta I_1$$

By way of generalization, it is necessary for simultaneous excitation with n wavelengths to take n+1 images $I_0$ to $I_n$, each with its own phase and/or frequency of excitation modulation. Phase images (image phase: $\phi_i$) with phase coding of the excitation wavelength ($\phi_j$) give the following images which contain the image information of the pseudo-con focal section ($C_j$) and of background ($B_j$), which image information is excited by the respective jth wavelength:

$$I_0(x) = \sum_{j=1}^{n} C_j(x)\cdot\cos(k\cdot x + \phi_j + \varphi_0) + B_j(x)$$

$$I_1(x) = \sum_{j=1}^{n} C_j(x)\cdot\cos(k\cdot x + \phi_j + \varphi_1) + B_j(x)$$

$$I_2(x) = \sum_{j=1}^{n} C_j(x)\cdot\cos(k\cdot x + \phi_j + \varphi_2) + B_j(x)$$

$$\ldots$$

$$I_n(x) = \sum_{j=1}^{n} C_j(x)\cdot\cos(k\cdot x + \phi_j + \varphi_n) + B_j(x)$$

The resulting equation system having the following form $$\begin{pmatrix} c_{11} & c_{12} & \ldots & \ldots \\ c_{21} & c_{22} & \ldots & \ldots \\ \ldots & \ldots & \ldots & \ldots \\ c_{n1} & c_{n2} & \ldots & c_{nm} \end{pmatrix} \cdot \begin{pmatrix} C_1 \\ C_2 \\ \ldots \\ C_n \end{pmatrix} = \begin{pmatrix} I_1 - I_0 \\ I_2 - I_0 \\ \ldots \\ I_n - I_0 \end{pmatrix},$$

where $c_{ij}(x)+\cos(k\cdot x\cdot\phi_j+\phi_i)-\cos(k\cdot x+\phi_j)$, can be solved for the sought for image information from inside the pseudo-confocal section separately according to the individual excitation wavelengths by known mathematical methods (e.g., Cramer's rule), Further, the image information from outside the pseudo-confocal section that is excited by all wavelengths can accordingly be determined according to the following equation:

$$\sum_{j=1}^{n} B_j(x) = I_0(x) - \sum_{j=1}^{n} C_j(x)\cdot\cos(k\cdot x + \phi_j + \varphi_0).$$

Analogous relationships apply when the frequency is used, instead of or in addition to the phase, for coding the various wavelengths and/or images. The coefficients $c_{ij}$ are suitable for modification.

The coefficients $c_{ij}$ can be determined by the measurement methods described in the following, regardless of whether phase and/or modulation frequency are/is used for image coding and wavelength coding, respectively. The coding frequency and the coding phase are determined (e.g., by means of a test object such as a glass plate or a mirror) for a reference wavelength (for example, 488 nm) for purposes of calibration. For this purpose, the periodic structure is imaged on the test object and measured by the detector, and the coding frequency and coding phase are measured and accordingly determined for a fixed image phase at the location of the specimen. The coding phases and coding frequencies of the other wavelengths can now be measured relative to this reference for a fixed image phase. In a possible arrangement, the phase coding is realized by dispersion (parallel offset) in a plane-parallel plate P which simultaneously serves as a support for an amplitude grating (structure S) arranged in front of it in the illumination direction (see FIG. 7A). A slight, wavelength-dependent parallel offset in the plane vertical to the axis of rotation and to the optical axis results when polychromatic excitation light passes through the plane-parallel plate P which is inclined slightly about axis A (inclination: $\gamma$; thickness: d):

$$\Delta x(\lambda)=d\cdot(\sin\gamma-\cos\gamma\cdot\tan\beta(\lambda)), \text{ where } \beta(\lambda)=\sin^{-1}((\sin\gamma)/n(\lambda)).$$

Figure 8:
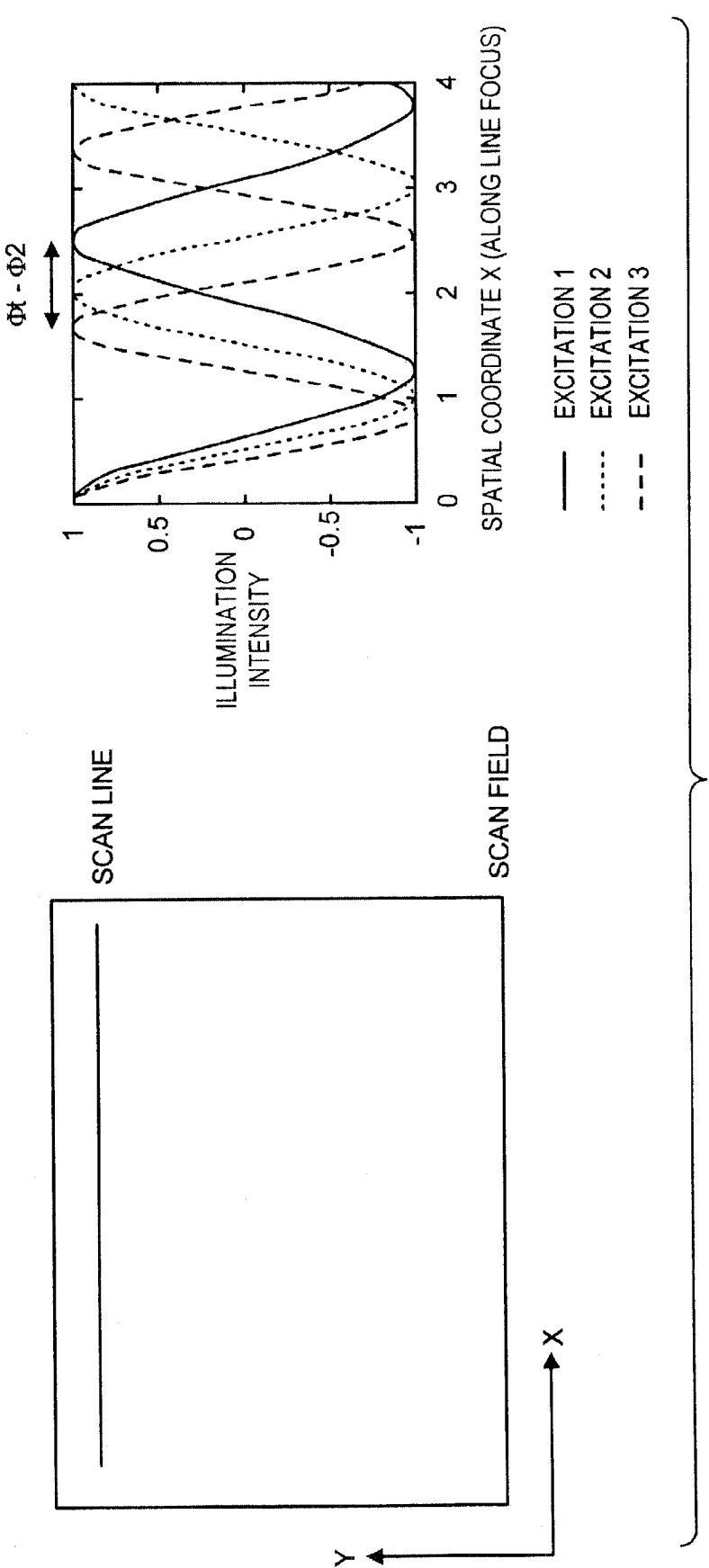
FIG. 8 shows schematically a line focus in a scan field in which phase positions of the amplitude modulations are presented.

When the plate is located in an intermediate image plane (see FIG. 9A) of the microscope arrangement, this offset is expressed as the phase shift between the amplitude modulations of the individual excitation line foci. FIG. 8 shows schematically a line focus in a scan field, in which the phase positions of the amplitude modulations for, e.g., three different excitation wavelengths are shown on the right-hand side of the diagram. The x-axis of the diagram corresponds to the coordinate along the line focus. Only a section of the scan line is shown on the right-hand side of FIG. 8 to illustrate the coding phases.

A phase displacement of 5 degrees is sufficient for reliably separating the signals excited by the corresponding wavelength. Table 1 shows the coding phases for a concrete example.

Table 1: Phase displacement for important laser lines by dispersion in a BK7 plate having a thickness of 10 mm with an amplitude grating of 50 lines/mm, The plate is inclined by 5 degrees relative to the normal; for the reference wavelength of 488 nm, this gives a parallel offset of approximately 300 μm relative to the optical axis.

| Wavelength (nm) | Relative offset (μm) | Phase displacement for 50 lines/mm (degrees) |
|---|---|---|
| 458 | 1.08 | 19.5 |
| 476 | 0.36 | 6.5 |
| 488 | 0 | 0 |
| 514 | −0.56 | −10.1 |
| 532 | −0.82 | −14.8 |
| 543 | −0.95 | −17.1 |
| 633 | −1.47 | −26.5 |
| 1064 | −2.75 | −49.5 |

An arrangement for wavelength-dependent phase displacement (phase coding) uses an optical grating which is inserted in a pupil plane of the microscope arrangement, for example, in the scanner.

Advantageous arrangements for fluorescence and DIC image display, for example, are described in the following without restrictions with regard to transferability to other optical contrast methods.

Arrangement 1 Structured Illumination with Single Scan Line

Figure 9A:
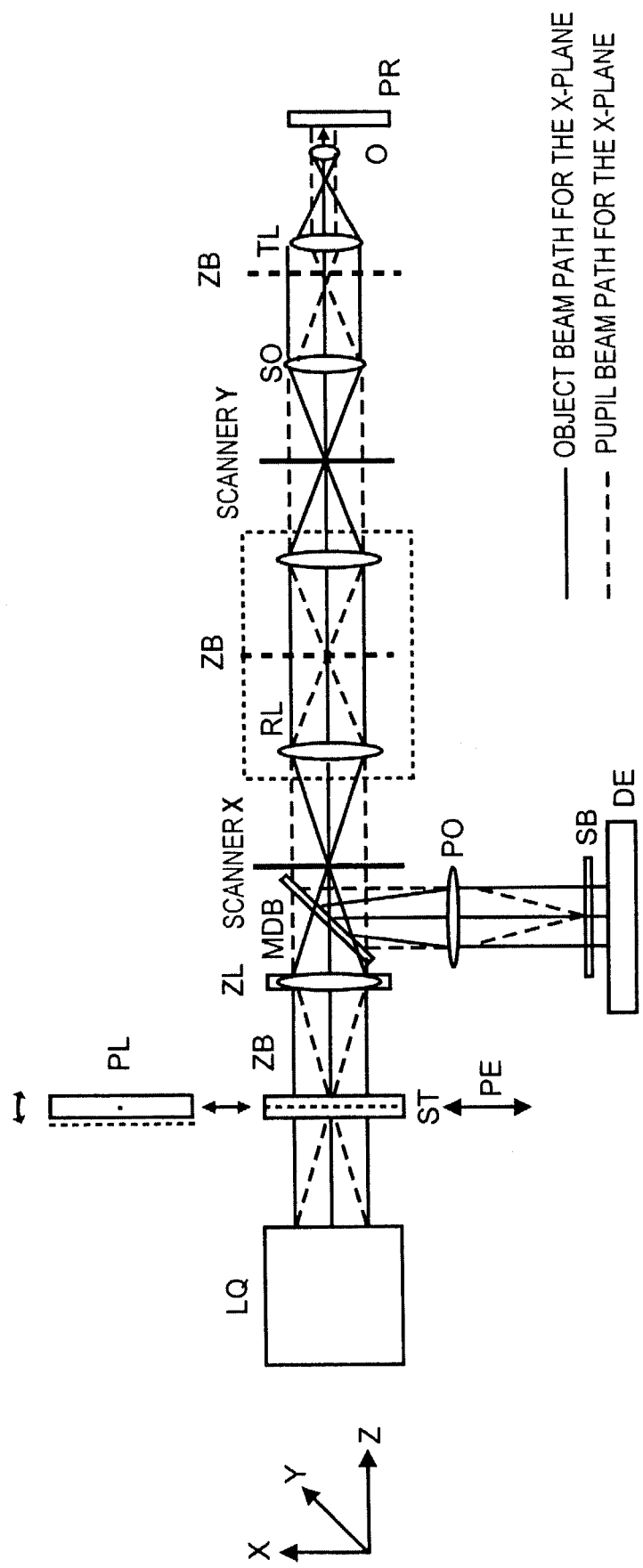
FIGS. 9A–C show a first arrangement of a structured illumination with single scan line.

A first arrangement is shown in FIG. 9. The pupil beam path of the microscope arrangement is shown in dashes. The object beam path is indicated by solid lines. In FIG. 9A (xy-plane), light from the light source (LQ) is shaped into a line focus in an intermediate image plane (ZB), for example, by a cylindrical lens (ZL), the pupil plane of the microscope arrangement being located in the focal length of the cylindrical lens (ZL). An element (ST) which produces an amplitude modulation along the scan line is located in an intermediate image plane in front of or behind the cylindrical lens (illustrated in front of the cylindrical lens). This clement ST is a transmission grating, for example. As is shown by way of example in FIGS. 7B/7D, the change in periodicity runs in the X-direction at right angles to direction (Y) of the grating lines which are shown schematically as black bars. A displacement in this X-direction, for example, with the positioning unit PE as is shown in FIG. 9, enables a change in the phase position. A displacement of the structure according to FIG. 7D in the Y-direction (displacement not shown) results in a variation of the frequency of the amplitude modulation for adapting the optical section thickness (see the following) or for changing the modulation frequency during the recording of the individual images for calculating the optical section image. Tilting around a center of rotation located in the optical axis and an axis of rotation in the Y-direction likewise generates this displacement. A rotation of the grating about an axis of rotation in the Z-direction, which coincides with the optical axis, for example, likewise generates (see FIG. 16) a phase displacement which has different results when imaging a plurality of spatially separate lines on the specimen (line running in X-direction).

The structured scan line is subsequently imaged in the specimen (PR) via a main beam splitter (MDB) and a scanner (y), which moves the scan line vertical to the line (y-coordinate) and is again located in a pupil of the microscope arrangement, by means of the scan optics (SO), the tube lens (TL) and the objective (O). The relay optics (RL) image the focal point of the cylindrical lens (ZL) on the scanner (y). In special arrangements according to the prior art, the relay optics can also be dispensed with. For example, they can be omitted when the distance is shortened between the two scanners x and y or when the scanners x and y are replaced by a gimbal-mounted individual scanner. In principle, the cylindrical lens can also be replaced by a cylindrical mirror whose focal point lies on the scanner (X). The cylindrical mirror is arranged at 45° in the xz-plane shown in FIG. 9C. In this plane, the mirror also has a focusing effect. Further, the beam path is angled by 90° to the light source by the mirror. This is shown schematically in FIG. 9C.

The emission light collected by the objective (O) is split from the excitation light, for example, by means of the main beam splitter (MDB). Subsequently, the light from the specimen is focused by means of imaging optics (PO) with con focal detection through a slit diaphragm (SB) (slit position in longitudinal direction in Z-direction in the drawing), so that fluorescence occurring outside of the focus is suppressed. With non-descanned detection, the diaphragm can be omitted. A line detector or surface detector (DE) (position of line in Z-direction) is located behind the slit diaphragm and detects the fluorescence in a spatially resolved manner (along the line focus). In addition, an emission filter (not shown) can be provided for suppressing the excitation radiation in the detection beam path after the main beam splitter (MDB). The line focus is scanned in one spatial direction by the galvo-scanner (y). If the x-scanner is not used for adjusting the image phase, it stays in its zero position.

Figure 9B:
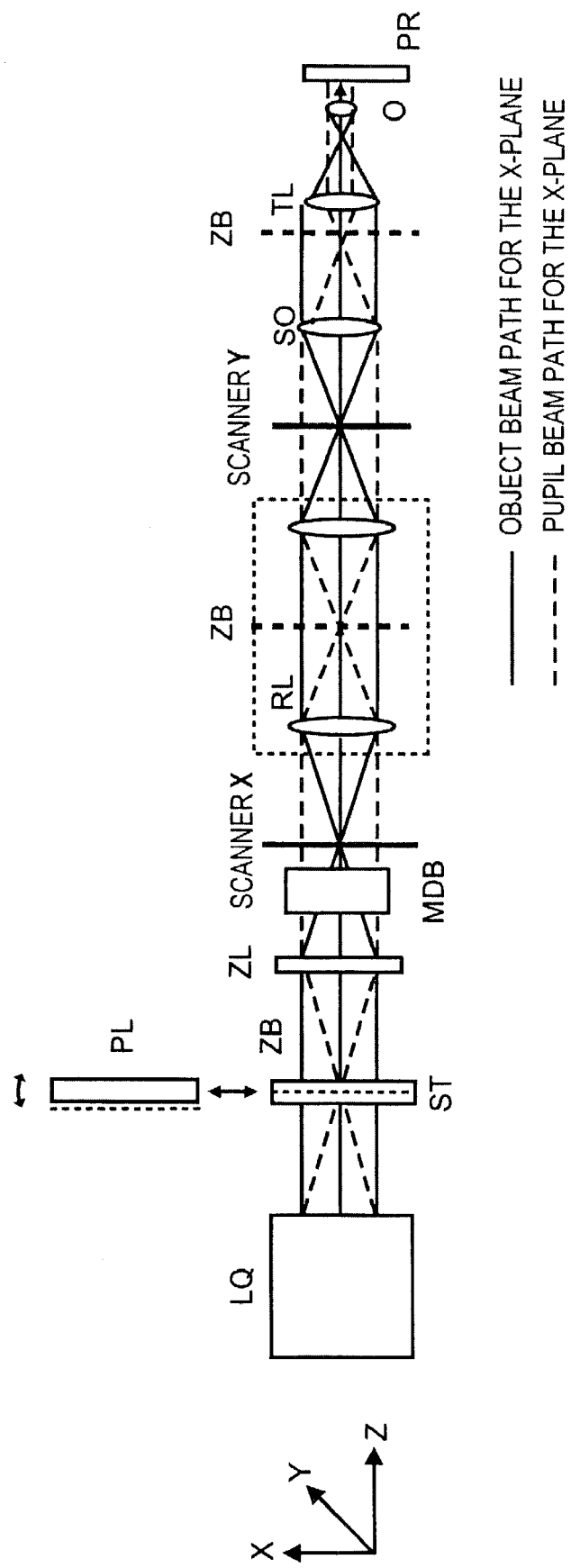
Figure 9C:
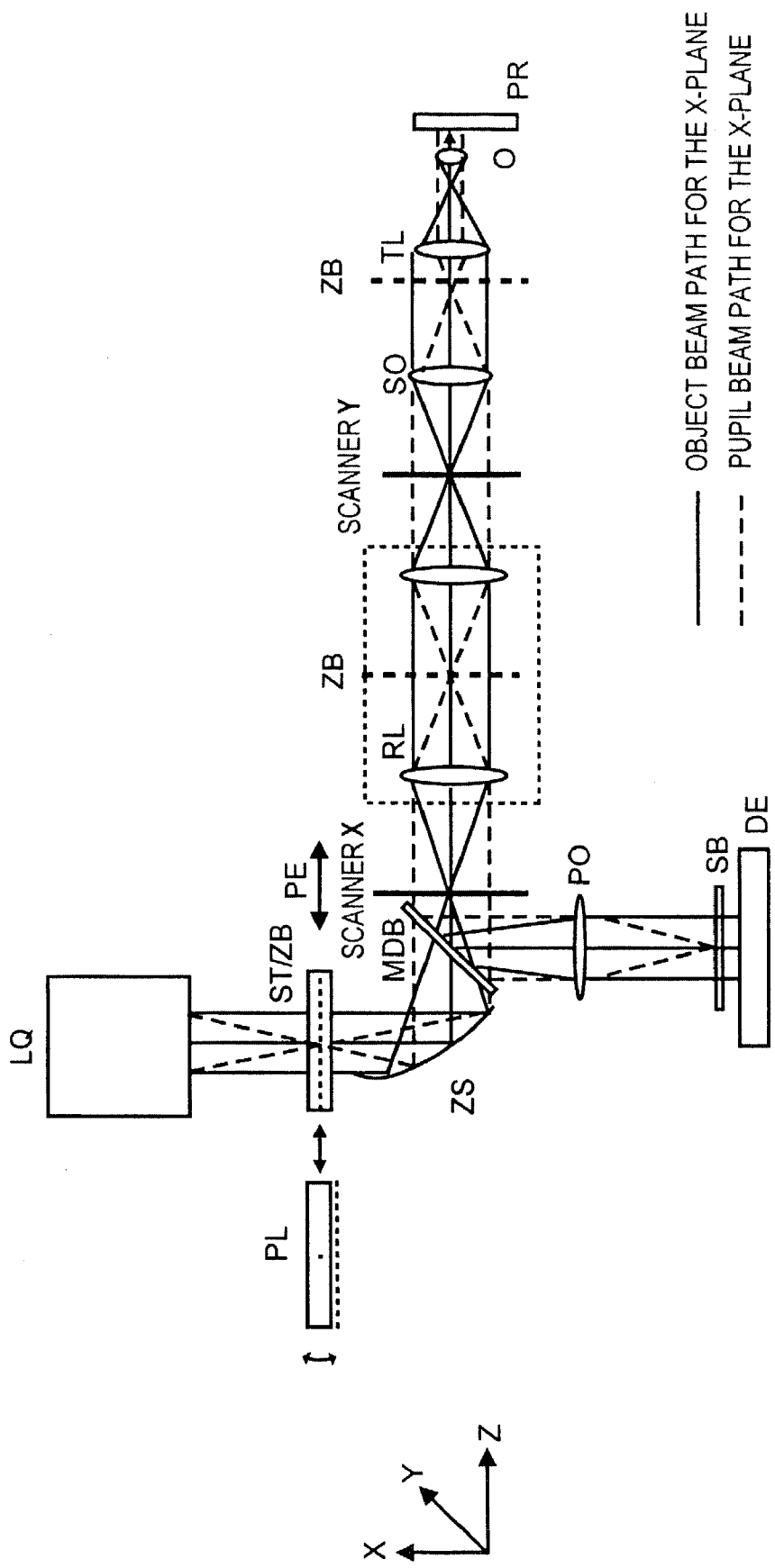

FIG. 9B shows the same arrangement, but mirrored by 90 degrees (YZ-plane), Instead of a line on the specimen, a focus point is shown on the specimen in this spatial direction due to the cylindrical lens (ZL) which is not effective in this direction.

Figure 19:
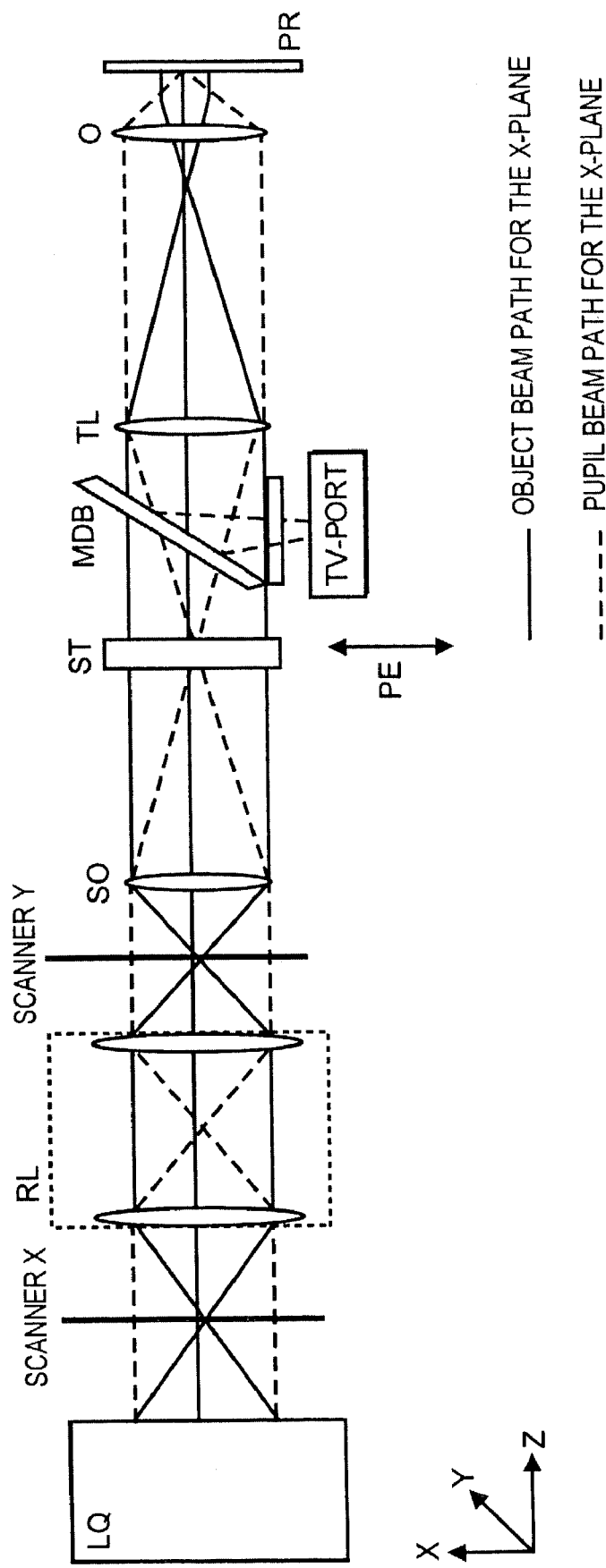
FIG. 19 schematically shows a structure used in an intermediate image plane which is arranged after the scanners in the direction of the specimen in a punctiform specimen interaction.

In principle, the slit diaphragm can also be omitted. This is useful, above all, when the imaging of the fluorescence is not descanned via the scanner but is to be carried out directly on a CCD camera or a gated camera for spatially resolved measurement of the fluorescence lifetime (LaVision, Picostar). The CCD camera sees an intermediate image plane ZB, e.g., in the intermediate image plane between the TL and SO of the microscope arrangement. In a microscope according to the prior art, it is connected to a TV port (FIG. 19, TV port position). In addition, a CCD camera can be used in the transmission beam path of the microscope arrangement (e.g., FIG. 1 instead of T-PMT). The excitation radiation transmitted by the specimen can accordingly be detected with confocal resolution. In addition, confocal DIC imaging is also possible. For this purpose, according to the prior art, the DIC prism is arranged in the objective pupil between TL and objective O. Further, the image obtained in this way by DIC can be superposed with the images that were generated by signals reflected, scattered and/or emitted by the specimen to form one image, The calculation of the con focal section is carried out, for example, by taking at least two phase images (see FIG. 4 or the following text). The illumination intensity of the lines in the at least two phase images varies periodically—for example, sinusoidally—in x-direction due to the structure ST. The relative image phase when using three structured lines is displaced by 120-degree phases, The three phase images are generated in sequence, i.e., three images are scanned successively by means of the y-galvo-scanner (y). The structure (ST) can be a transmission grating, for example. The displacement of the image phase can be carried out, for example, with a positioning unit (PE) to which the transmission grating is coupled, so that every location of the specimen to be examined can be observed with varying brightness. Further, the adjustment of the image phase can be carried out as in FIG. 7A with a wavelength by means of a plate (PL) which is mounted in rotatable manner, the structure being arranged in front of the latter or impressed on it. The plate is to be arranged for this purpose in an intermediate image plane of the microscope arrangement as is shown in FIG. 9. The plane-parallel plate used for this purpose is located in an intermediate image plane; the structure ST (shown in FIG. 7B) is preferably arranged directly on the plate.

In another arrangement, the adjustment of the image phase can also be carried out by means of another galvo-scanner (X). The scanner (X) adjusts the image phase by displacing the scan line in x-direction. This has the advantage that it enables switching between a point-scanning LSM and a line-scanning LSM with structured illumination by inserting (swiveling in or sliding in) the cylindrical lens (ZL) and the transmission grating coupled with a detection-side beam deflection for switching from a point detector to a line detector (DE). If the scanner X is not used for adjusting the image phase, it stays in its zero position (i.e., is switched off).

Figure 10A:
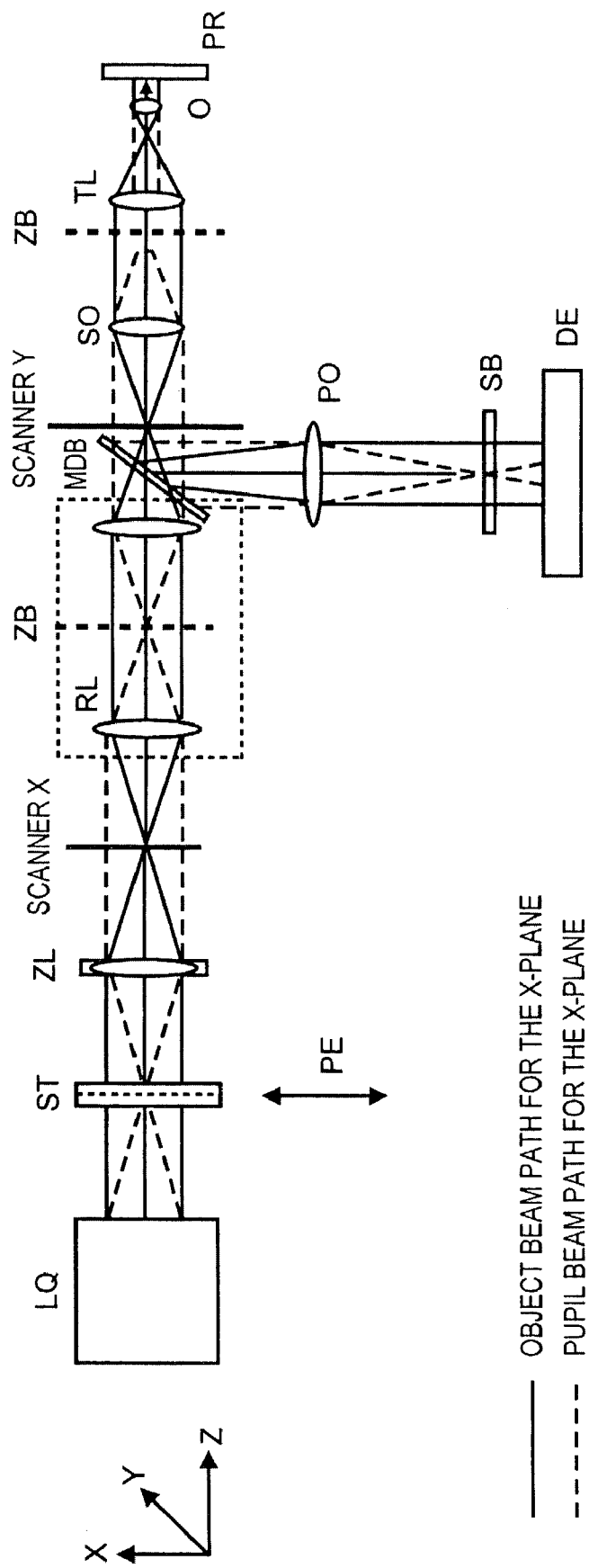
FIGS. 10A, B show schematically a structured illumination with single scan line and coding of the modulation phrase or modulation frequency.

Arrangement 2 Structured Illumination with Single Scan Line and Coding of the Modulation Phase or Modulation Frequency A second arrangement uses different coding phases depending on the excitation wavelength used in the structuring of the scan line. The signals of the fluorescence excited by the individual wavelengths can accordingly be digitally separated, FIG. 10A schematically shows a possible construction in the XZ-plane, Light of different wavelengths from the light source (LQ) undergoes amplitude modulation by means of a structure (ST). The structure is located in an intermediate image plane of the microscope arrangement. The structure is arranged so as to be displaceable via a positioning unit (PE), so that the structure can be displaced along the scan line and different image phases can be adjusted. Subsequently, the structured light is shaped in cylindrical optics (ZL) to form a line in the pupil plane of the microscope arrangement. For this purpose, the cylindrical lens (ZL) is arranged at the distance of its focal length from the pupil (scanner X), Further, the adjustment of the image phase can be carried out by the scanner (X) which is located in a pupil plane of the microscope arrangement.

Figure 10B:
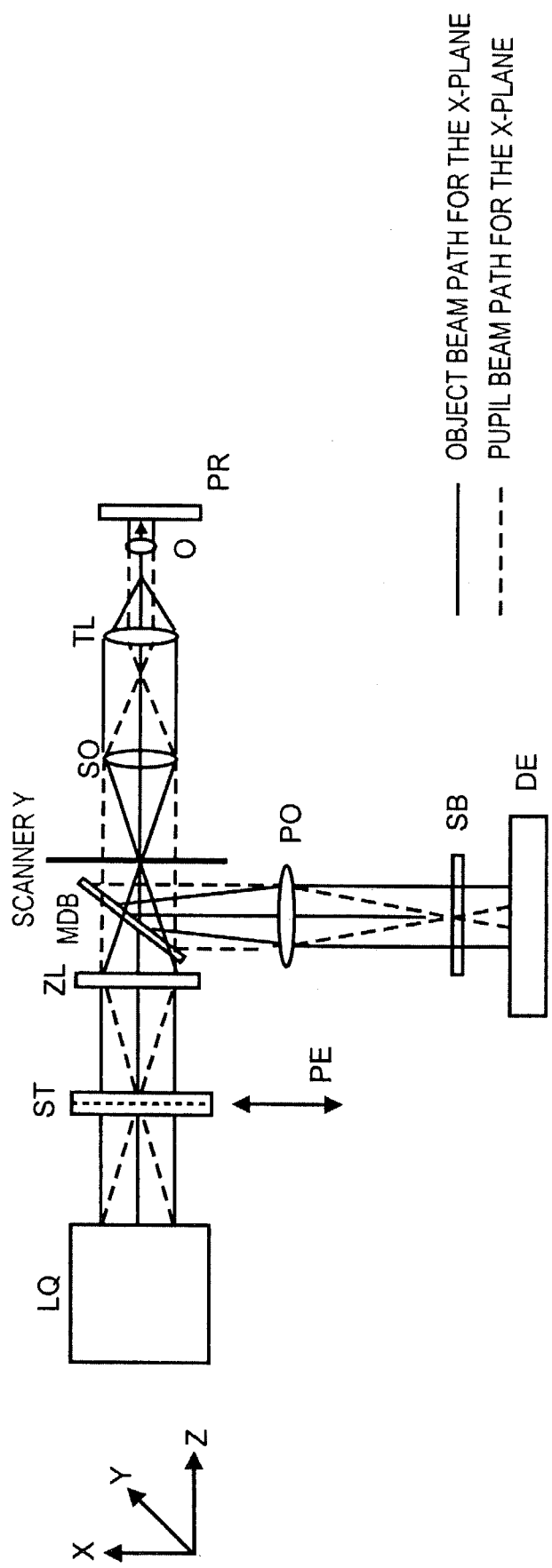

FIG. 10B shows a simplified arrangement with only one scanner (Y) in the XZ-plane. The adjustment of the image phase is carried out by the positioning unit PE.

After an amplitude modulation has been impressed on the scan line, the radiation passes through an element in which the structure is displaced in a wavelength-dependent manner (ST) and the coding phase is accordingly varied in a wavelength-dependent manner. A possible arrangement for phase coding was already described with reference to FIG. 7A. The plane-parallel plate used in this case is situated in an intermediate image plane; the periodic structure ST (shown in FIG. 7B among others) is preferably arranged directly on the plate.

Figure 11:
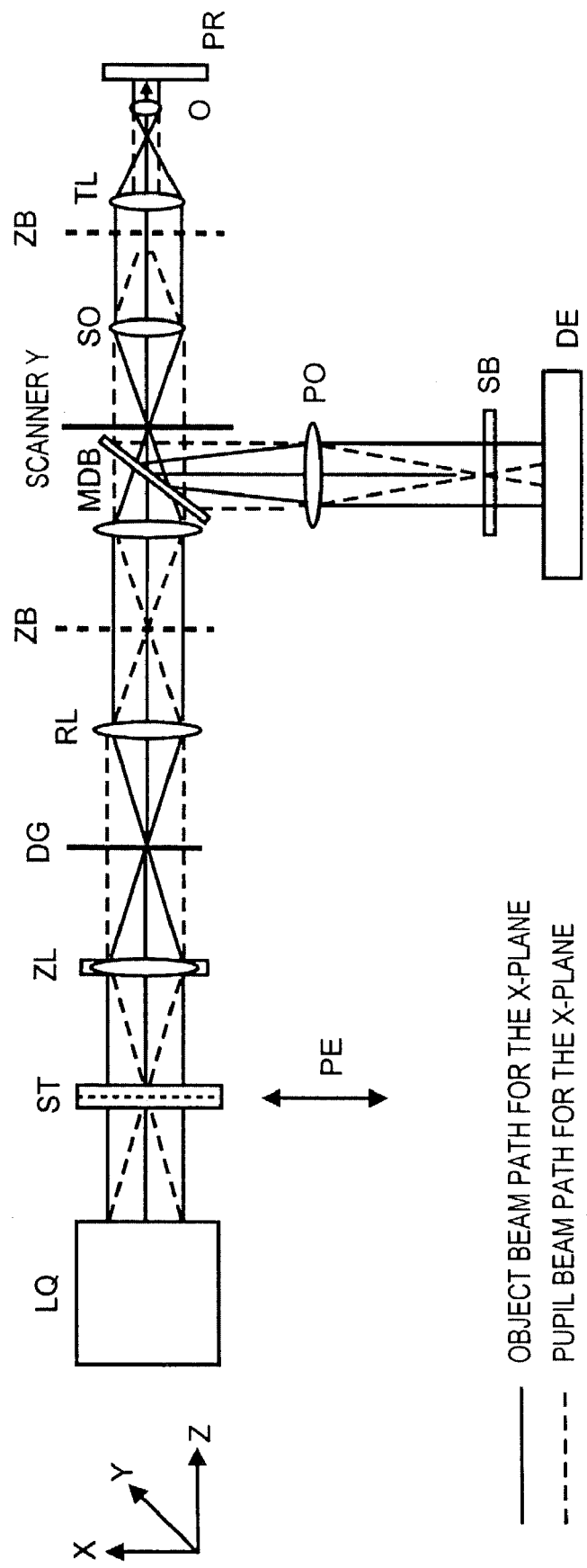
FIG. 11 illustrates schematically another arrangement where the optics is shown in the XZ plane.

Following the phase coding or frequency coding of the amplitude modulation, the excitation radiation reaches the specimen via the main beam splitter (MDB), the Y-scanner, the scan optics (SO), the tube lens (TL) and the objective (O), The Y-scanner scans the scan line to record a phase image in the y-coordinate. The fluorescence excitation is carried out with the corresponding wavelengths depending on the dyes used. The modulation frequency and modulation phase of the scan line is transferred to the fluorescence signal in this way depending on the excitation wavelength. In descanned detection, the fluorescences are collected by the objective and arrive at the main beam splitter (MDB) via the tube lens, scan optics and Y-scanner. This main beam splitter (MDB) separates the fluorescence from the excitation radiation. Following this, the fluorescence is imaged on a line detector (DE) through a slit diaphragm. Additional blocking filters may be placed in front of the line detector to suppress the excitation wavelength. The slit diaphragm can be dispensed with particularly in multiphoton excitation. The separation of the individual signal components that have been generated by the various wavelengths and the calculation of the optical sections are carried out based on the algorithm described above, for example, using the coding phases at the same modulation frequency, wherein the coding phases of the individual wavelengths have been determined beforehand with test objects such as plane mirrors. Accordingly, regions which have been dyed with different dyes can be made visible separately, Another arrangement uses a dispersive element (DG), e.g., a transmission grating, which is located in a pupil plane of the microscope arrangement. The optics diagram in FIG. 11 is shown in the XZ-plane. The transmission grating displaces the individual scan lines within the drawing plane corresponding to their wavelength (only one WL shown). Accordingly, a different phase position of the modulation structure ST (coding phase) is impressed on the individual scan lines corresponding to their wavelength. The displacement of the image phase is carried out by means of the positioning unit (PE) and the modulation structure S for every wavelength with identical step size. This ensures that the image phase displacement is 120° for every excitation wavelength, for example, when three phase images are taken.

Advantageous arrangements for generating the frequency coding and adapting the optical resolution are described more fully in the following.

The effective pinhole size, i.e., the optical section thickness for the individual wavelengths, can be adapted by changing the modulation frequency for every excitation wavelength.

FIG. 7C schematically shows a device for wavelength-dependent adjustment of the modulation frequencies which is advantageously installed, instead of the structure ST, in arrangements 1 and 2 (as shown in FIG. 9, for example) in an intermediate image plane of the microscope device. In so doing, a polychromatic light source is spatially split into its spectral components by a dispersive element (DG1). Following this, the spectral components are made axially parallel with a first lens (lens 1, focal length f), i.e., DG1 lies in the focal point of the lens, The structure (ST) with which the amplitude modulation is carried out is located in the imaging-side focal plane. A possible construction of the structure with linear dependence of the frequency in y-direction is shown schematically in FIG. 7D.

The splitting into lines L1, L2, L3 which is carried out according to FIG. 7C produces different modulation frequencies on this periodic structure through the different positions of the lines in y-direction.

Thus, when a spatial splitting of the polychromatic light source is carried out with linear dependence on the wavelength, e.g., by a transmission grating, then, with a suitable grating design, the modulation frequencies of the individual spectral components also change depending on the wavelength. In this way it can be ensured, e.g., that the same optical section thickness is realized at different wavelengths. The individual spectral components are subsequently spatially superimposed again by means of a second lens (lens 2, focal length f, which need not be the same as the focal length of lens 1) and another dispersive element (DG2, e.g., transmission grating, which need not be identical to DG1). The beam expansion can be controlled or monitored by adapting the focal lengths of lenses 1 and 2 and the illumination of the microscope objective can accordingly be optimized. The following advantageous variants of the invention result from a structure of the kind mentioned above.

a) A different change in phase can be generated in a defined manner (after prior calibrating measurement) for the individual lines by means of a displacement of the structure ST in x-direction, wherein, in the different phase positions, a complete scanning of the specimen by means of the respective line is carried out and wavelength-dependent section images are calculated. The section thickness can be changed by means of a defined shift in frequency by displacement in y-direction.

b) By means of (at least one) displacement in y-direction, the modulation frequency is changed in a defined manner and section images can accordingly be calculated by repeated scanning at different modulation frequencies for the individual wavelengths. Further, a frequency coding and/or phase coding can be generated for different wavelengths via the different modulation frequencies of the structure with imaging of all wavelengths on a common line (see arrangement 4).

Instead of the structure with continuous change in modulation frequency in y-direction which is shown in FIG. 7D, a structure (see also FIG. 16) which is composed of a plurality of partial structures of different modulation frequencies can be used. This has the disadvantage that the structure is adjusted only for fixed excitation wavelengths. However, in the simplest case, different gratings ST, each with a different modulation frequency, can also be swiveled into the arrangements 1 and 2.

In another arrangement, not shown, the radiation, after structuring, passes an element in which the structure is increased in a wavelength-dependent manner, so that the modulation frequency varies in a wavelength-dependent manner, i.e., a frequency coding is carried out. In a first arrangement, the scan line is split into its individual wavelength components by dichroic beam splitters and a wavelength-dependent increase is subsequently impressed in the partial beam paths with a telescope having zoom optics for adjusting the increase. The individual scan lines are superimposed again by means of additional dichroics. Alternatively, in another arrangement, special diffractive elements which generate a wavelength-dependent increase in the scan line can also be used.

At the start, the scan line has a specific coding frequency of amplitude modulation depending on the wavelength that is used. The displacement in the image phase is earned out by means of the positioning unit (PE) and the displaceable structure ST for every wavelength with an identical step size. This ensures that the image phase displacement for each excitation wavelength is 120°, for example, when three phase images are taken. Instead of taking phase images, the optical section can be calculated from two images in which the modulation frequency is different per excitation line in the two images. The change in modulation frequency for all wavelengths or one wavelength can advantageously be carried out by taking the two images at different positions in the y-direction of the transmission grating according to FIG. 7D, It can be ensured by means of the arrangements described above, for example, that the axial optical resolution of the microscope is identical for different wavelengths. Accordingly, colocalization measurements are possible with a linear scanner. In addition, the effective pinhole can be increased, for example, in case of very weak fluorescence signals, by displacing the structure in y-direction, see FIG. 7D, in this case, downward. While this reduces the optical resolution, the signal-to-noise ratio can be improved.

In addition, the above-described zoom optics, not shown, serve to compensate for the chromatic longitudinal error of the imaging optics and, accordingly, to ensure that the optical slice is carried out in the same object plane. For this purpose, a lens of the individual zoom optics is misaligned slightly depending on the microscope objective employed, so that the beam for the individual wavelengths at the output of the zoom optics impinges divergently or convergently on the objective pupil and the focus can accordingly be shifted in axial direction depending on the excitation wavelength, i.e., made to coincide for all excitation wavelengths.

Figure 12:
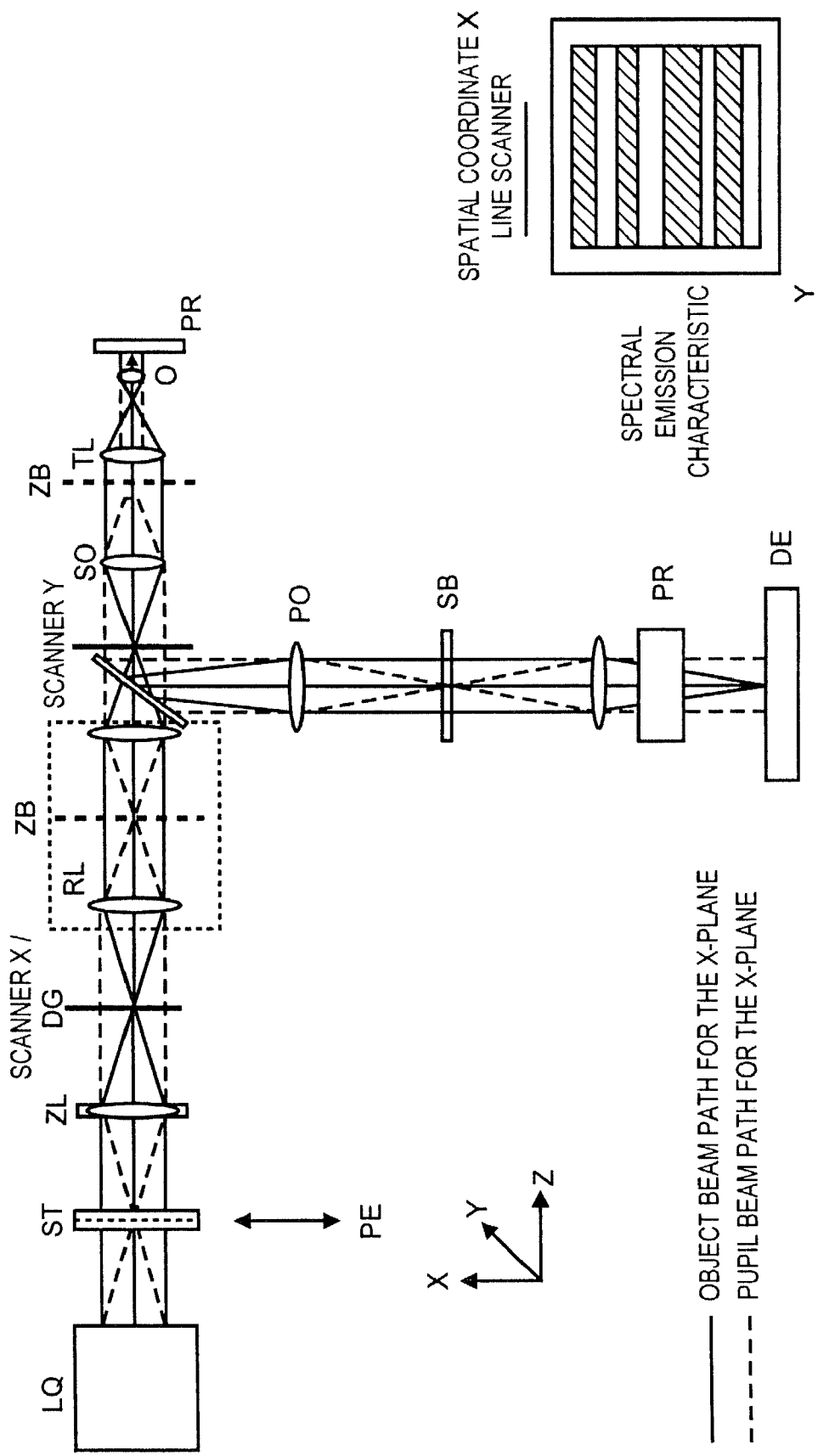
FIG. 12 illustrates schematically the detection diagram of a CCD surface of the multispectral line scanner in the XZ plane.

In addition to constructions 1 and 2, another dispersive element (PR) can be used for additional spectral splitting of the fluorescence signals vertical to the illumination line (multispectral line scanner). FIG. 12 shows the detection diagram of a CCD surface of the multispectral line scanner in the XZ-plane. The structured emission signals for the respective wavelengths are imaged in the x-direction of the detector (DE).

The adjustment of the image phase can also be carried out in this case by the X-scanner as an alternative to the displacement of the phase position by means of PE.

An image is taken for every scan position of the scan line, as is shown for different detection wavelengths. The freely programmable control of selected detector elements (lines) and the combination of detector elements of a column of the detector matrix allows a flexible selection of spectral regions of the fluorescence emission. For this purpose, a plurality of lines of the detector in which different fluorescence signals are imaged corresponding to their wavelength can be connected together electronically. The multispectral detection of the fluorescence emission can be combined again with the structured illumination. For this purpose, the line-shaped excitation is structured in addition, e.g., by means of a transmission grating (ST). In this connection, a complete scan process of the scan line is carried out by detecting the wavelength distribution corresponding to the imaging in FIG. 12 and further scanning processes are earned out by changing the image phase of the grating structure. Since a plane plate PL has been tilted in a defined manner, for example, for determining a wavelength-dependent offset, the change in phase position can be carried out, e.g., through displacement by PE at a constant tilting angle. The depth contrast can be optimized again by sequential detection of images of structured objects with different image phases of excitation and subsequent calculation. FIG. 12 shows the combination of a multispectral line scanner (spectral splitting is carried out in the y-plane, that is, into the drawing plane) with structured illumination via the structure ST, wherein the phase coding is earned out again by a tilted plane-parallel plate (not shown) which is displaced vertical to the optical axis or by a dispersive element (see above). The image phase is varied sequentially. The different spectral components are detected in parallel by means of CCD arrays.

The slit diaphragm (SB) which serves in this case as an entrance slit for the spectral splitting can be omitted in case of descanned detection in the line scanner. While this reduces spectral resolution, it considerably simplifies apparatus because, otherwise, displaceable individual slit diaphragms would have to be used.

Figure 13:
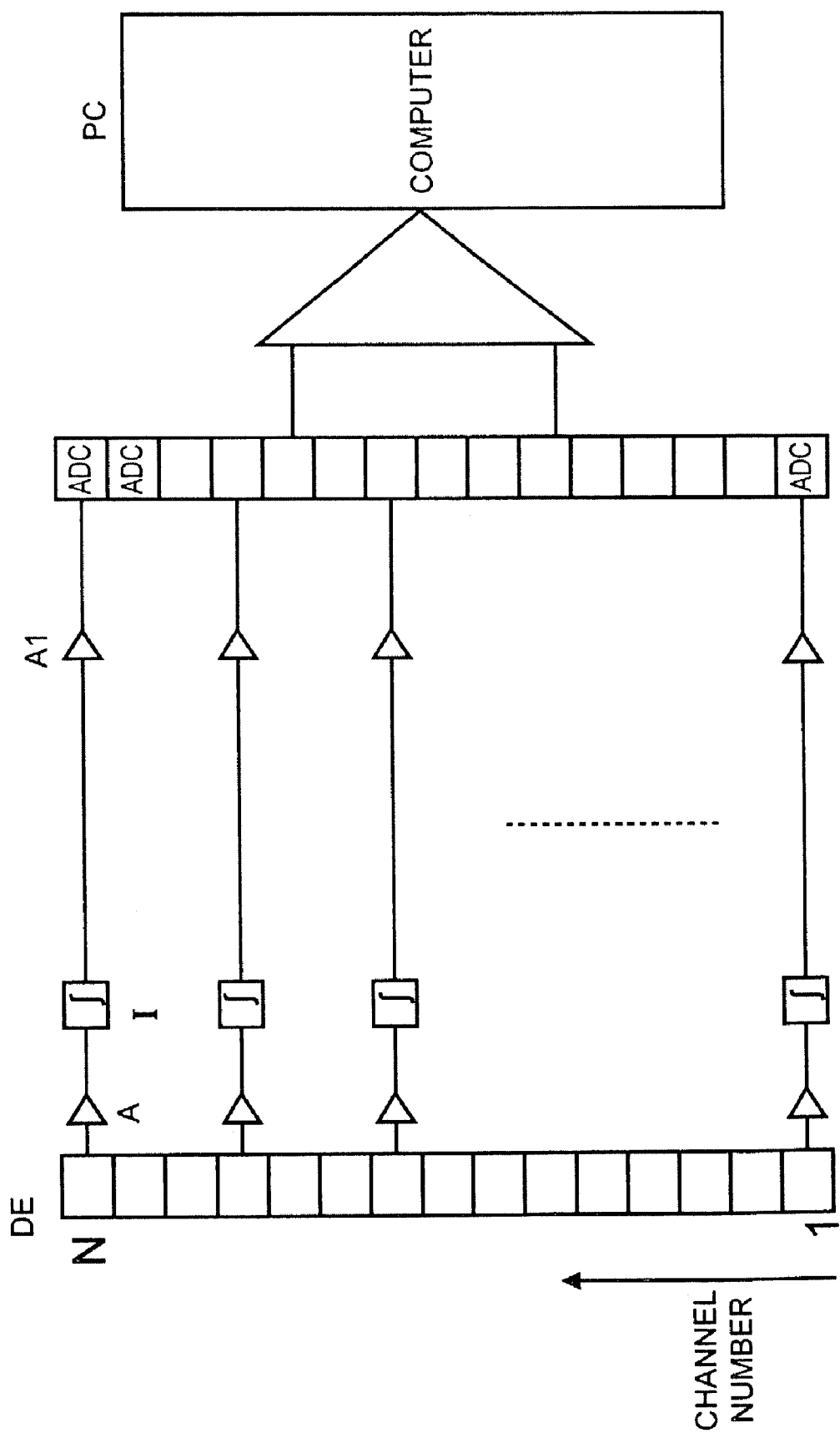
FIG. 13 schematically shows the construction of the electronics for detecting the signals with a line detector.

FIG. 13 shows schematically the construction of the electronics for detecting the signals with a line detector. For this purpose, signals of the detector K1–N are amplified by means of a current-voltage converter (A) and are subsequently integrated (I) during the pixel holding time. After further amplification for level matching to an analog-to-digital converter (ADC), these signals are converted into digital signals in the ADC and are transferred to a computer (PC). Detection with a CCD matrix is known from the technical literature.

Figure 14:
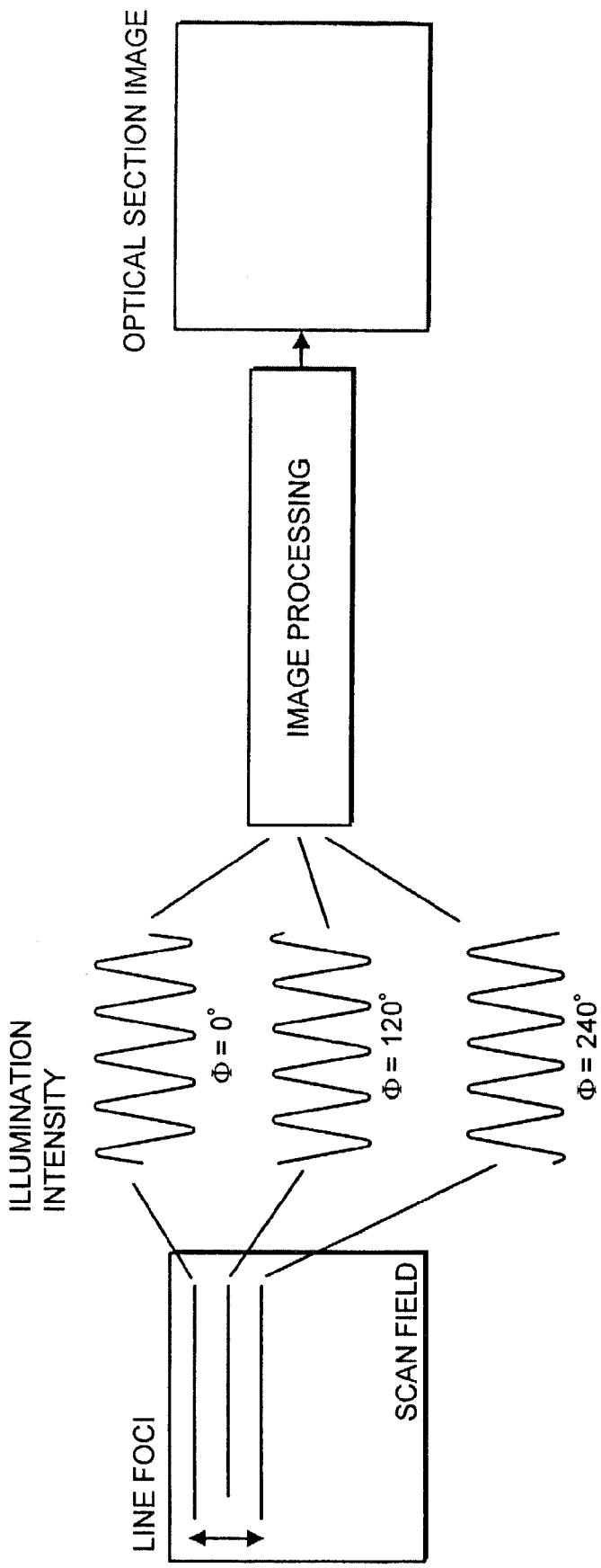
FIG. 14 shows schematically the detection of the stripe images quasi-simultaneously when using three lines.
Figure 15:
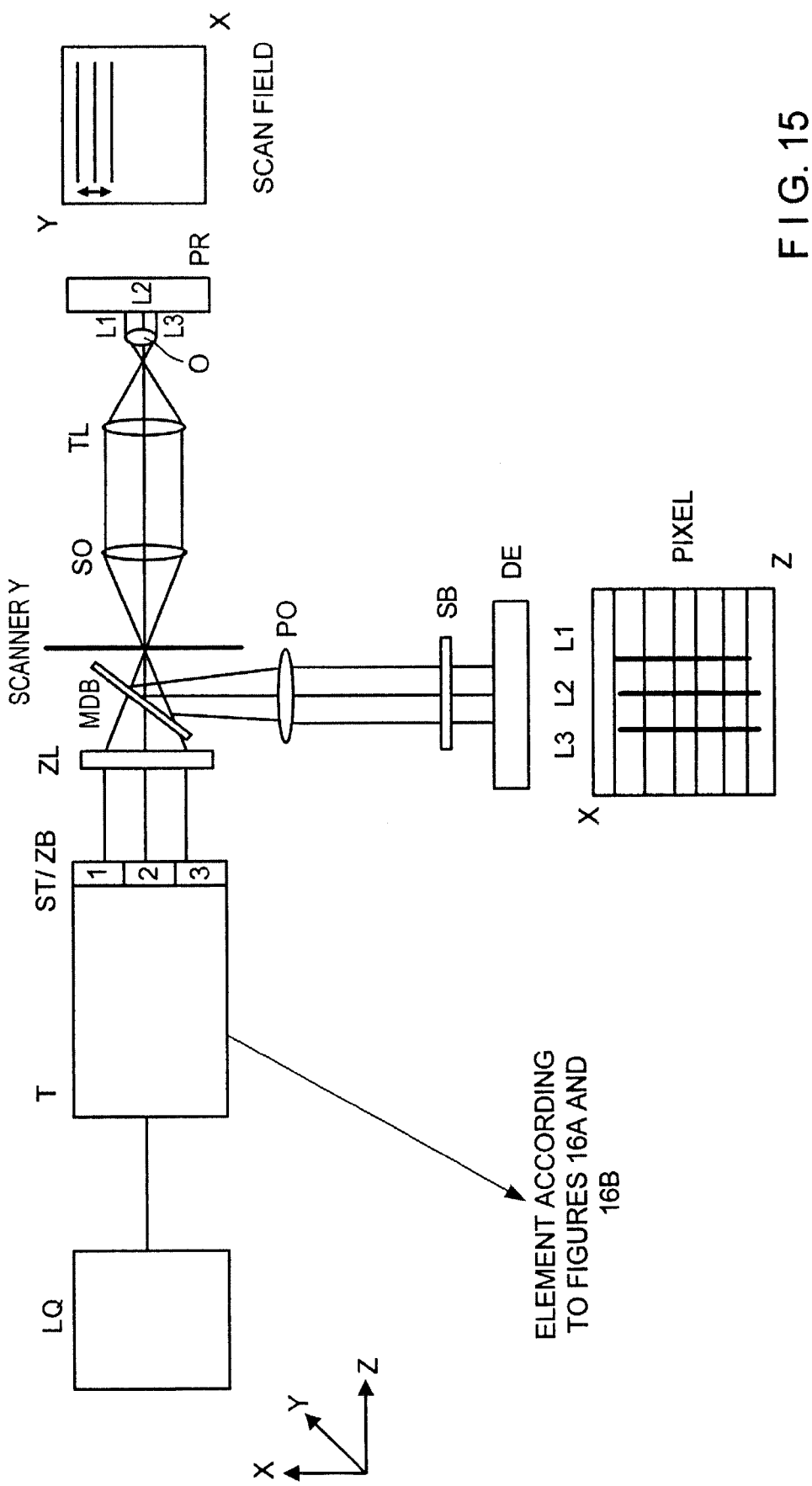
FIG. 15 schematically shows the optical construction of the FIG. 14 application in the XZ plane.
Figure 16A:
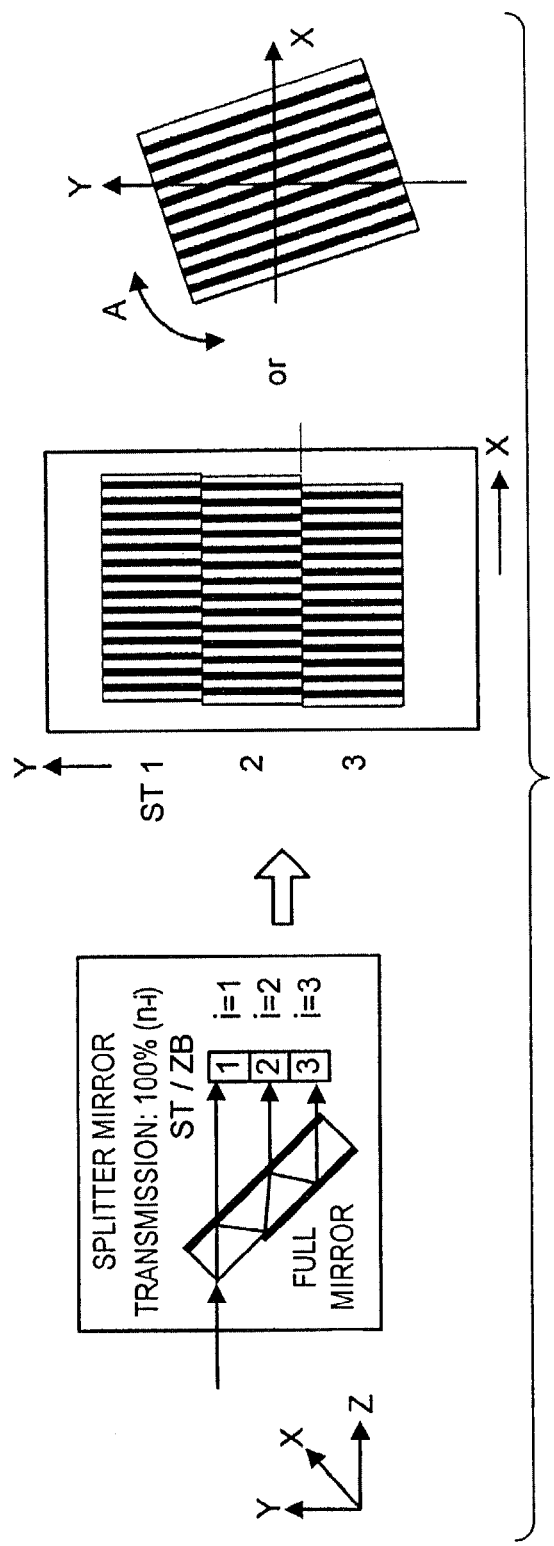
FIG. 16A shows a special grating structure for the quasi-simultaneous recording case.
Figure 16B:
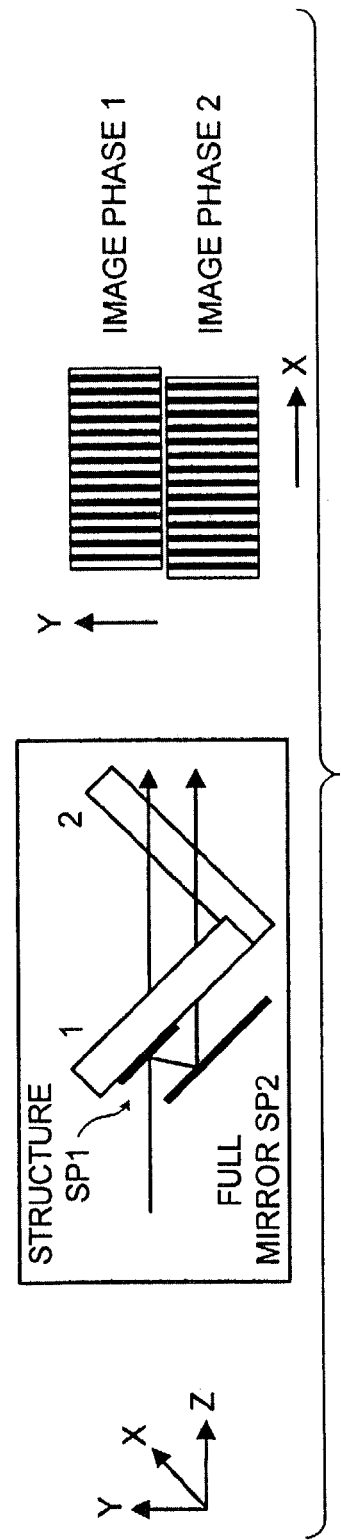
FIG. 16B shows a second arrangement for generating a double line focus.

Arrangement 3 Structured Illumination with Quasi-Simultaneous Recording of Phase Images The detection of the stripe images can also be earned out quasi-simultaneously in that a plurality of lines (e.g., L1, L2, L3), instead of one line, are imaged in the specimen in parallel, wherein the intensity structure (image phase) is displaced, e.g., by 120°, in a manner analogous to FIG. 4, for example, when using, e.g., three lines (FIG. 14), Accordingly, all of the information for evaluating the data is generated already in the one-time scanning of the specimen, FIG. 15 schematically shows the optical construction in the YZ-plane. The focal points along the y-axis of the line foci are shown. The excitation light can be split by a beam splitter arrangement (T), Two embodiment forms of the beam splitter arrangement (T), which in this case is arranged in front of the cylindrical lens, are shown in FIGS. 16A–B. The first arrangement, in cooperation with the cylinder lens, generates a plurality of discrete line foci with two mirrors arranged in parallel, wherein the first mirror is a full mirror and the second mirror is a partially transmitting mirror. The transmission of the partially transmitting mirror is adapted to every partial beam (i) and results from 100%/(n−1), where n is the total number of individual foci. Subsequently, the components (i) arrive separately in a special grating structure (ST) which is shown schematically in FIG. 16A, The partial gratings are modulated in this structure with a defined phase offset. Instead of the structure composed of partial gratings, a transmission grating according to FIG. 7B which is rotated as shown in FIG. 16A can also be used, so that the phase offset of the structure can be adjusted deliberately for the individual scan lines with identical modulation frequency in each instance. The calibration of the device, i.e., the determination of the modulation frequency and the phase positions of the scan lines, is carried out according to the method described above. The structure is located in an intermediate image plane of the microscope arrangement. The splitter arrangement can also be used, for example, in a pupil plane of the microscope arrangement. In this connection, both mirrors are tilted toward one another so that a plurality of line foci are formed again.

The second arrangement in FIG. 16 (FIG. 16B) is a special arrangement for generating a double-line focus. The arrangement again uses two mirrors (SP1 and SP2) arranged in parallel, one of which mirrors (SP1) carries the structure ST itself The structure reflects at the points of low transmission. The structure is arranged in the intermediate image of the microscope arrangement. Two lines whose amplitude modulations are in exactly opposite phase occur at the output of the splitter. The line 1 accordingly has an amplitude modulation that is exactly shifted by 180° relative to line 2. The structure is applied to glass plate 1. When a plurality of wavelengths are used, (lie wavelength-dependent parallel offset in y-direction is compensated through the plane-parallel glass plate by a second glass plate of the same thickness which is arranged at an angle of 90°. In addition, the entire splitter unit (T) is tilted slightly about the y-axis for generating the phase coding described above. A displacement of the structure (ST) can be dispensed with in both arrangements. The scanning movement of the Y-scanner is carried out over the image field actually being examined, so that every point on the specimen to be examined is illuminated once by a line of a different phase position of the structure. This arrangement is particularly advantageous for examining rapidly changing specimens because movements or rapid changes in the specimen no longer have an interfering effect on the measurement and the maximum image recording speed of the line scanner is not reduced by the sequential data acquisition. The detection of the lines which are excited in parallel is carried out with a matrix detector which, in the case of three lines, for example, is a three-line detector. Alternatively, a line detector on which all lines separated on the specimen are detected simultaneously can also be used. The separation of the information of every line can be carried out by means of the algorithm described above on the basis of different modulations (in phase and/or frequency) of every line.

Figure 17:
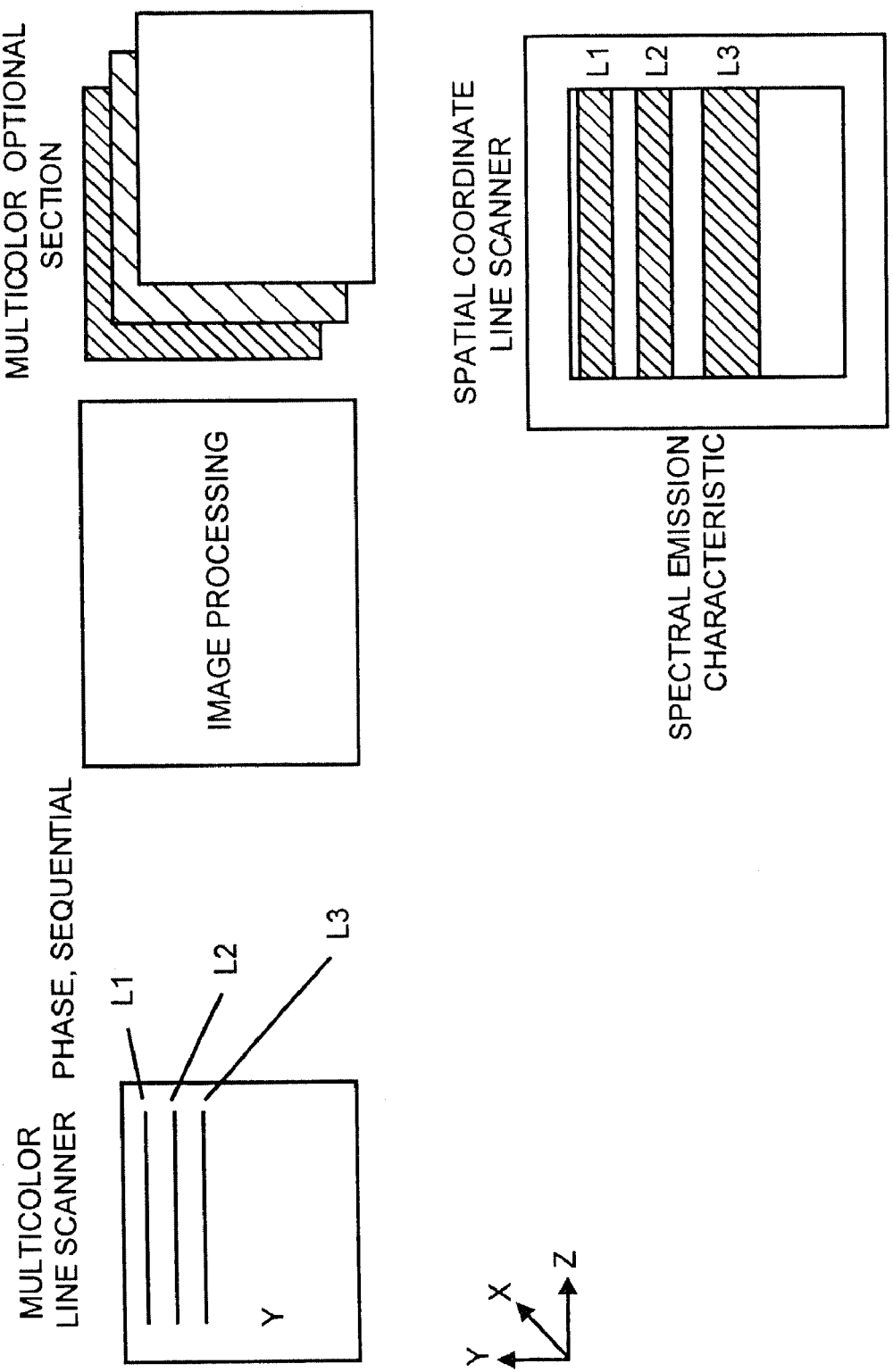
FIG. 17 is directed to a structural illumination with quasi-simultaneous multispectral excitation where a plurality of parallel excitation lines of different wavelengths are generated by dispersive element.

Arrangement 4 Structured Illumination with Quasi-Simultaneous Multispectral Excitation In a fourth arrangement, a plurality of discrete excitation wavelengths arc formed so as to be spatially separated in different scan lines (e.g., with three laser lines: L1, L2, L3 in x-direction) in the specimen. For this purpose, a plurality of parallel excitation lines of different wavelength are generated (see FIG. 17) by a dispersive element (PR) (e.g., transmission grating, grating lines in x-direction) and are moved over the specimen by means of the y-galvo-scanner (y) and subsequent optical imaging in such a way that every point in the scan field under consideration is scanned at least once by every line. The optical construction is shown schematically in the YZ-plane in FIG. 18. The beam centroids of the line foci are shown in the drawing.

The splitting of the fluorescence signals by the excitation is again carried out with the main color splitter (MDB). The fluorescence signals which have been generated by the different excitation lines arrive on different positions L1-L3 in z-direction of a matrix detector with slit diaphragms arranged in front of the latter in x-direction, wherein the axis at right angles to the illumination line corresponds to the corresponding wavelength of the fluorescence. The axis along the illumination line on the matrix detector corresponds to the spatial coordinate.

In addition, a phase coding or frequency coding can also be carried out corresponding to arrangements 1 and 2. For example, for phase coding the structure (ST) is tilted about the Y-axis. Frequency coding can be carried out, e.g., with the special structure shown in FIG. 7D. When using a phase coding or frequency coding, the spectral components can again be detected simultaneously with a detector matrix which simultaneously detects all scan lines. In the simplest case, a CCD line with rectangular pixels (or joined lines) can be used for this purpose, the longer sides of the pixels advantageously being oriented in direction z (see FIG. 18), so that, for example, the scan lines L1 to L3 are detected jointly by the detector line. The separation of the signals which have been excited by the different scan line foci is then carried out again according to the algorithm described above.

The advantage of these arrangements consists in that the individual scan lines need no longer be detected separately on a detector array, but can be detected by a one-dimensional detector.

Figure 18:
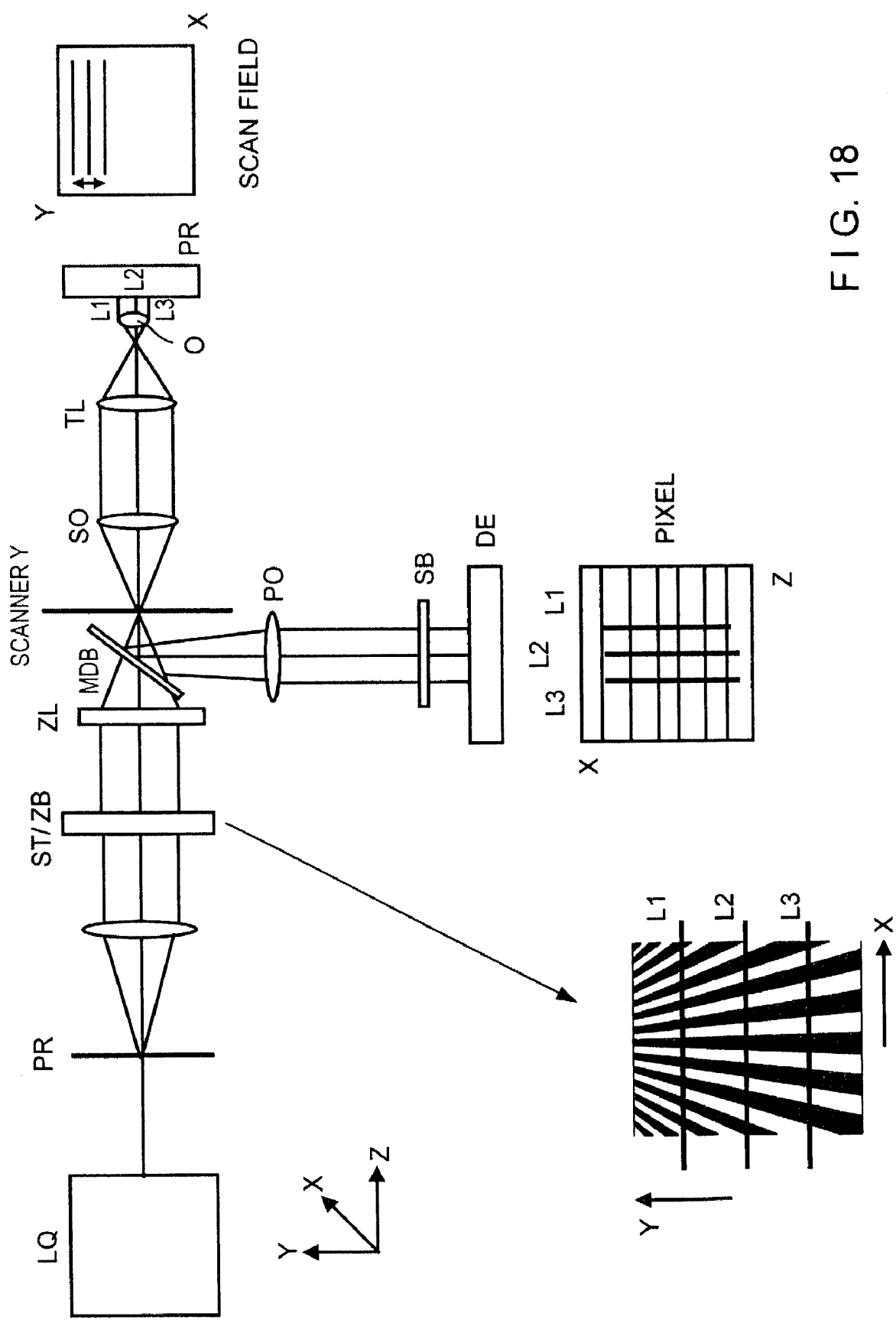
FIG. 18 schematically shows the combination of a multispectral line scanner with structured illumination.

In addition, another dispersive element can be used for additional spectral splitting of the fluorescence signals at right angles to the illumination line. The detection scheme for the multispectral line scanner shown in FIG. 12 can be used for this purpose. A spatial coordinate is imaged in one direction of the detector. The freely programmable control of selected detector elements (lines) and the combination of detector elements of a column of the detector matrix allows a flexible selection of spectral regions of the fluorescence emission. For this purpose, a plurality of lines of the detector in which different fluorescence signals are imaged corresponding to their wavelength are joined electronically. The multispectral detection of the fluorescence emission can be combined again with the structured illumination. For this purpose, the line-shaped excitation is additionally structured, e.g., by means of a transmission grating. The depth contrast can again be optimized by sequential detection of images of structured objects with different image phases and subsequent calculation. FIG. 18 shows the combination of a multispectral line scanner with structured illumination. The image phase is varied sequentially with various structures. The different spectral components are detected in parallel by means of a CCD array, for example. According to the prior art, a plurality of freely movable diaphragms arranged conjugate to the individual scan lines had to be used in this arrangement as confocal slit diaphragms; however, these can be dispensed with due to the structuring of the scan lines. The expenditure on technical apparatus is considerably reduced in this way.

Arrangements 5 Structured Illumination with Punctiform Specimen Interaction

Figure 1B:
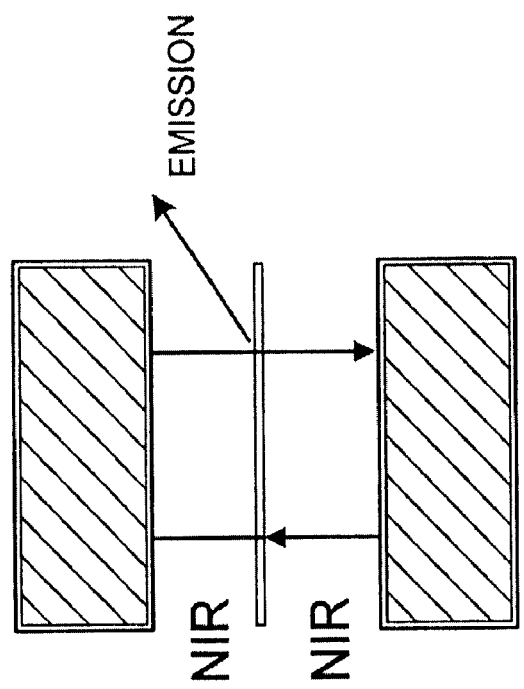
FIG. 1B illustrates multiphoton absorption in schematic form.
Figure 1A:
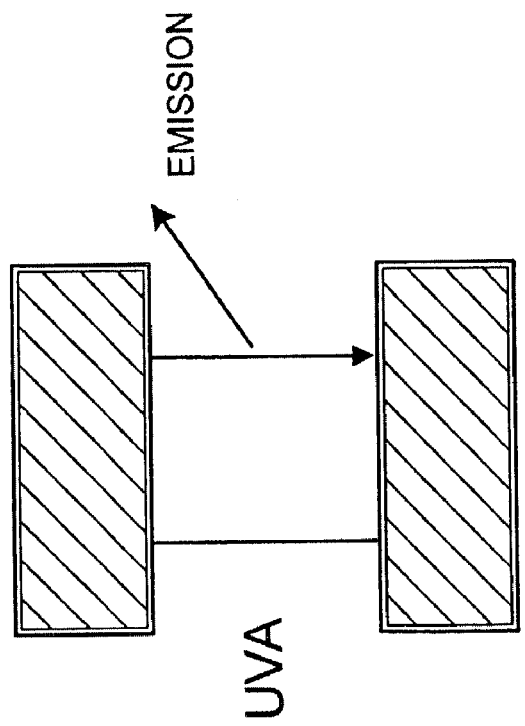
FIG. 1A illustrates in schematic form single photon absorption.

In a fifth arrangement, a punctiform excitation of the specimen is carried out instead of a line-shaped excitation of the specimen. For this purpose, the laser scanning microscope corresponding to FIG. 1 is operated according to the prior art. However, a structure (ST) corresponding to FIG. 19 is used in an intermediate image plane which is arranged after the scanners x and y in the direction of the specimen. The structure is imaged successively in the specimen by scanning in the x-direction and y-direction. The recording of phase images is carried out by means of a displacement of the structure with the PE, In addition, a quasi-simultaneous illumination can be carried out according to arrangements 3 and 4. A phase coding or frequency coding with the arrangements described above is transferable without restrictions. The advantage of this arrangement over a conventional point scanner is that the signal of the specimen can also be measured without descanning directly with a CCD camera. In this case, the confocal diaphragm is also omitted. A gated camera (Picostar, La Vision), for example, can also be used as a CCD camera. Accordingly, for example, time-resolved fluorescence recordings of confocal optical sections can be achieved. According to the prior art, this is only possible through the use of nonlinear specimen interactions.

However, a descanned punctiform detection or partially descanned detection (Stimson, et al., Rev. of Sc. Instr., (70), p3351, 1999) according to the prior art can also be carried out.

Further, by means of the phase coding or frequency coding, the signals of the specimen excited by different wavelengths can be recorded simultaneously with the described detection variants. Only one detector is needed for this purpose. Accordingly, the construction of a laser scanning microscope can be decisively simplified by this arrangement without limiting flexibility. By switching on the structure, it is possible to switch back and forth between a conventional laser scanning microscope and a laser scanning microscope with structured illumination.

A combination of methods 1–5 is likewise part of the invention. Further, a combination of the methods described above with parallel scanning methods according to the prior art is also possible without limitation. In these methods, a plurality of points or lines of identical intensity are imaged simultaneously as a matrix in the specimen (Buist, et al., J. o. Microscopy (192), p217, 1998; Nielsen, et al., J. o. Microscopy (201), p852, 2000). In this way, image recording rates can be further increased. Further, the specimen can be imaged by a table scanner or a scanner according to the prior art (e.g., Nipkow disk).

Figure 2:
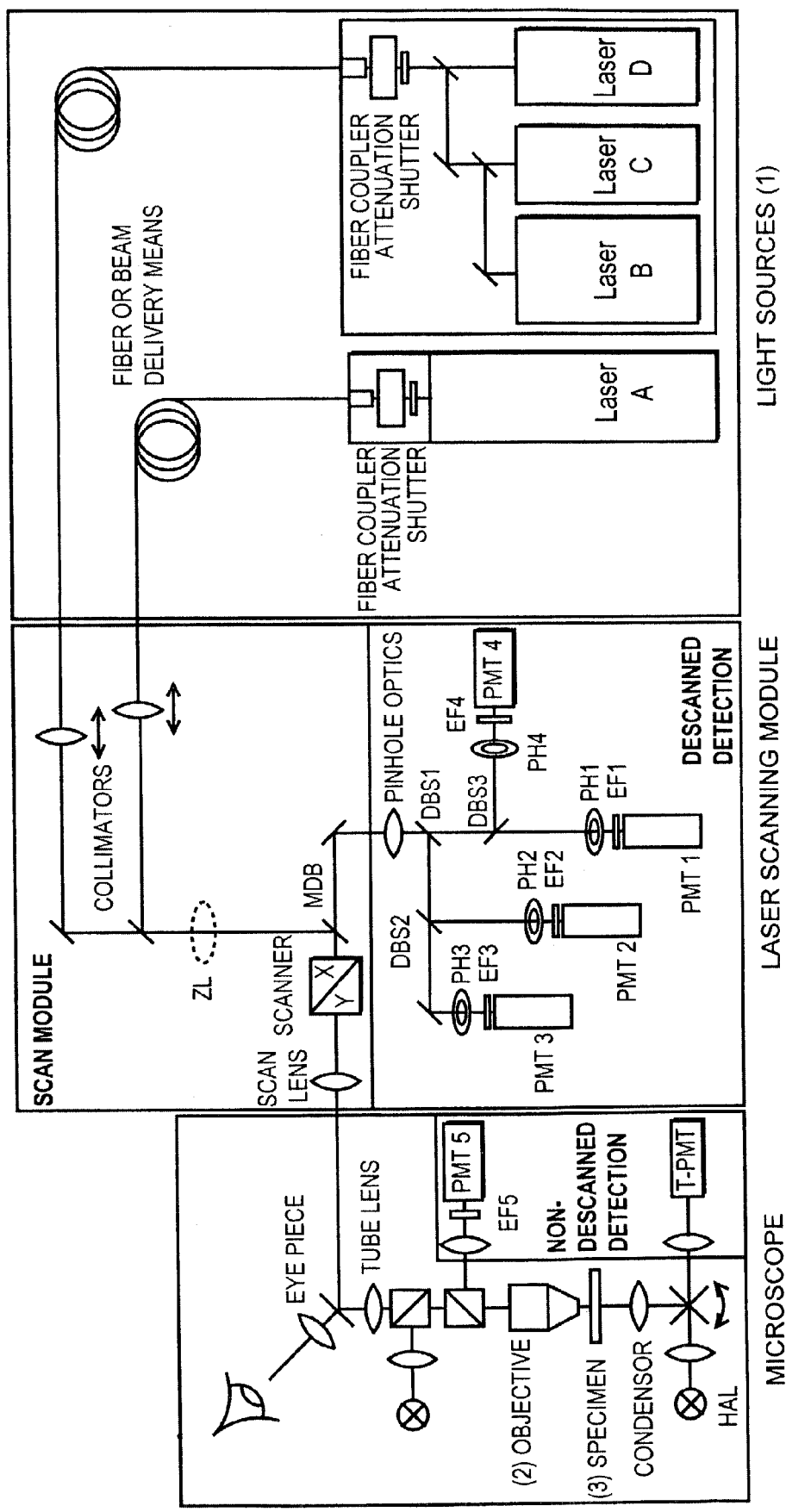
FIG. 2 illustrates a confocal laser scanning microscope (LSM)
Figure 3:
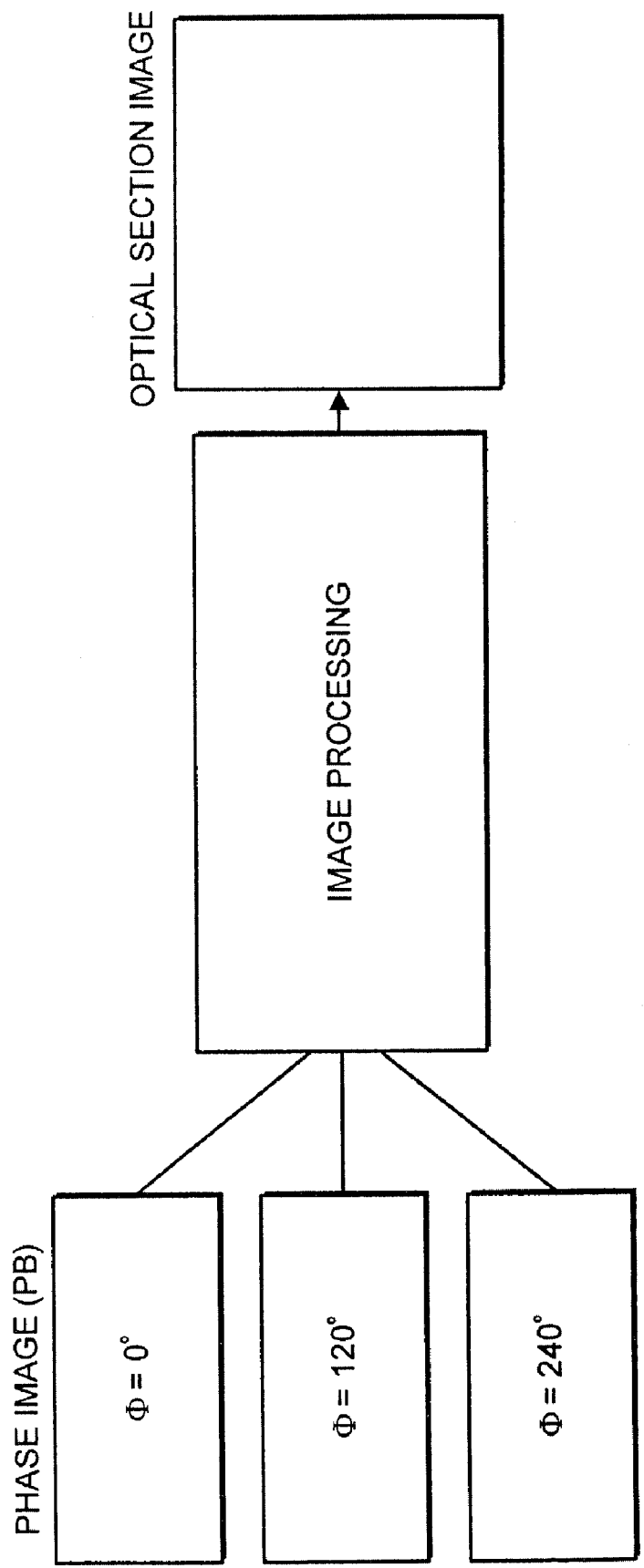
FIG. 3 illustrates structured illumination, a known method, in block diagram form.

The advantageous arrangements described above can also be used advantageously for examination of macroscopic specimens. Macroscopic specimens are used, for example, in screening active ingredients on a chip. The edge length of the scan fields amounts to several times 10 mm. These scan fields can be achieved, e.g., by increasing the scan angle of the galvo-scanner, by arranging the specimen in an intermediate image of the microscope arrangement, for example, in FIG. 2, or by a special objective arrangement (macro-objective) which images the intermediate image on the specimen in magnified manner.

An arrangement for increasing the fluorescence signal in two-photon or three-photon excitation by a factor of 1.5 or 2.5 is described in Hell, et al., Journal of Microscopy, Vol. 202, Part 3, June 2001, 457–463. For this purpose, a parallel excitation of the specimen is earned out in a plurality of foci which are illuminated three-dimensionally by the multiplex method. The illumination patterns generated by interference are shifted spatially over a period and the signal is recorded in a time-averaged manner over this period. The aim of this arrangement is to increase the fluorescence signal in multiphoton excitation. This method has no influence on the spatial resolution, i.e., the optical resolution is achieved by the nonlinear interaction in the individual specimen points according to the prior art cited above.

According to the invention, an interferometric superposition of at least two partial beams is used in this case for redistributing the average energy over the scan field to be examined. The redistribution of the average energy results in an increase in the fluorescence signal in multiphoton excitation. In addition, the interferometric superposition of the partial beams produces the above-described structuring of the scan line for increasing optical resolution. With the same fluorescence signal, the average output per specimen point can be reduced, so that there is reduced loading of the specimen to be examined. In addition, in comparison to the prior art, more specimen points can be examined simultaneously with the same output power of the laser, or lasers with lower output power can be used with the same quantity of specimen points.

The method according to the invention is accordingly particularly suitable for use in applications requiring a nonlinear specimen interaction, since they can he examined with reduced excitation intensity and, therefore, with less damage to specimens.

The principle of the method described herein consists in that a laser beam is divided into at least two partial beams of identical power by means of beam splitters or by pupil division, wherein the wavefronts of the partial beams enclose a small angle of typically less than 5° relative to one another. The n-partial beams are subsequently superimposed interferometrically in one of the specimens, so that a periodic fringe pattern results depending on the adjusted angle. The intensity $I_M$ of the fringe pattern along the coordinate x (excitation) can generally be described as follows:

$$I_M(x) = \left| \sum_{i=1}^{n} \sqrt{\frac{I_0}{n}} \cdot \exp(-i \cdot k \cdot \sin(\theta_i) \cdot x + \phi_i) \right|^2 \quad (0)$$

In this case, $I_0$ is the total intensity of the laser on the specimen which is split into equal parts on the n partial beams; $\theta_i$ are the angles and $\phi_i$ are the phase relationships between the partial beams with reference to an arbitrarily selected partial beam.

Different projection scenarios of the structure can be obtained by means of a phase shift (by changing the phase relationships $\phi_i$) of the structure vertical to the optical axis. The modulation frequency of the structured illumination is determined by the angles $\theta_i$.

Figure 20A:
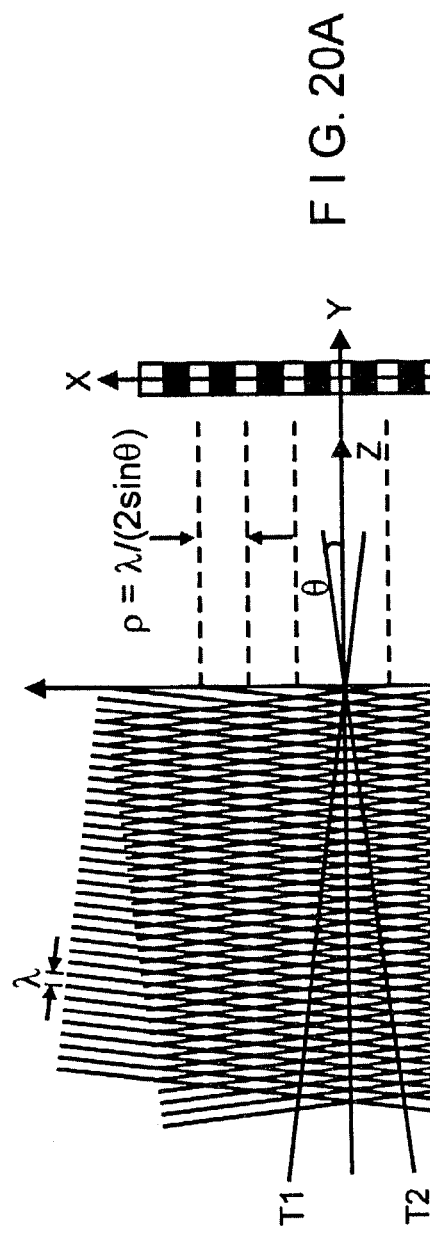
FIG. 20A schematically shows two plane wavefronts in the XY plane for examination of macroscopic specimens.

FIG. 20A shows two plane wavefronts in the X/Y plane—partial beams T1, T2 of wavelength λ which enclose an angle θ relative to the optical axis of the arrangement and interfere with one another.

A diffraction-limited periodic line-shaped intensity distribution results along X on the specimen by means of focusing in Y-direction, for example, through a cylindrical lens ZL in the specimen plane. Further, the line-shaped intensity distribution along X on the specimen can be carried out by diffractive or holographic elements according to the prior art ("Diffractive optics improve product design", Photonics Spectra, Laurin Publishing Co., Inc., September 1995). Further, a Powell lens, as it is called, such as is described in U.S. Pat. No. 4,826,299 can be used. The latter element generates a more homogeneous intensity distribution along the lens compared with the cylindrical lens. For this purpose, the Powell lens and the diffractive or holographic elements are arranged in a particularly advantageous manner, for example, in a pupil plane of the microscope device, between the light source and scanner.

For the general interferometric superposition of two partial beams of identical intensity (with total intensity $I_0$), each with a plane wavefront, the following intensity modulation is given vertical to the optical axis:

$$I_m(x) = I_0 \cdot [1 + \cos(k \cdot \sin(\theta) \cdot x + \phi)], \ldots \text{ where } \ldots k \approx 2\pi/\lambda \quad (1)$$

θ is the angle between the two wavefronts of the two partial beams. λ and $\phi$ are the wavelength of the partial beams and the phase position of the modulation frequency p. By changing the angle θ, the period of the modulation can be deliberately adjusted and a change in the optical section thickness can be carried out (see below). Further, the modulation frequency changes as a function of the wavelength that is used and the frequency coding described above can be earned out. The phase of the modulation frequency is determined by the phase relationship $\phi$ between the two partial beams. By varying $\phi$ in accordance with the preceding description, the image phases can be adjusted and a phase coding can be carried out.

Figure 20B:
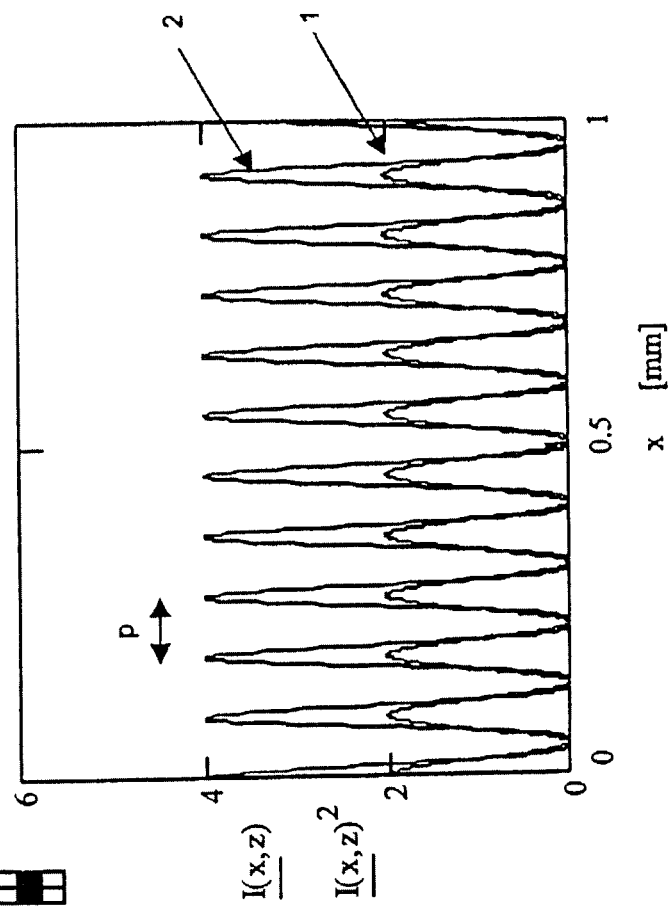
FIG. 20B shows the corresponding signal resulting along the scan line for a quadratic specimen interaction (two photon excitation)

The resulting intensity modulation for a linear specimen interaction (single-photon interaction) is shown in FIG. 20B (1). The respective intensity is plotted along the scan line (x coordinate) in the graph, where $I_0=1$ is assumed without limiting generality. The modulation is consinusoidal with period p and oscillates between 0 and 2 around the axis of symmetry 1.

The increase in the total signal with nonlinear specimen interaction (multiphoton excitation, generation of a higher harmonic) will be described more fully in the following with reference to the interferometric superposition of two partial beams.

When a nonlinear interaction with the specimen takes place, a detector measures the following signal $S_N$ resulting from the interaction:

$$S_N(x) = I_M(x)^N = [I_0 \cdot [1 + \cos(k \cdot \sin(\theta) \cdot x + \phi)]]^N, \quad (2)$$

where N is the order of nonlinearily. The corresponding signal $S_N$ resulting from this equation along the scan line is shown in FIG. 20B (2) for a quadratic specimen interaction N=2 (e.g., two-photon excitation), where $I_0=1$ is assumed without limiting generality. The modulation is periodic with period p. But the modulation is now asymmetric and oscillates between 0 and 4, since $\cos^2(x)$ is asymmetric to 1. This asymmetry increases for greater values of N.

The signal $S_N$ generated per period of intensity modulation is obtained by integrating the signal $S_N(x)$ in x-direction:

$$S_N = \int_0^p I_M(x)^N dx, \quad (3)$$

In comparison, the following specimen interaction results for a homogeneous distribution of the light intensity $I_0$ along the scan line in direction x:

$$F_N = \int_0^p I_0^N dx = I_0^N \cdot p \quad (4)$$

Figure 21:
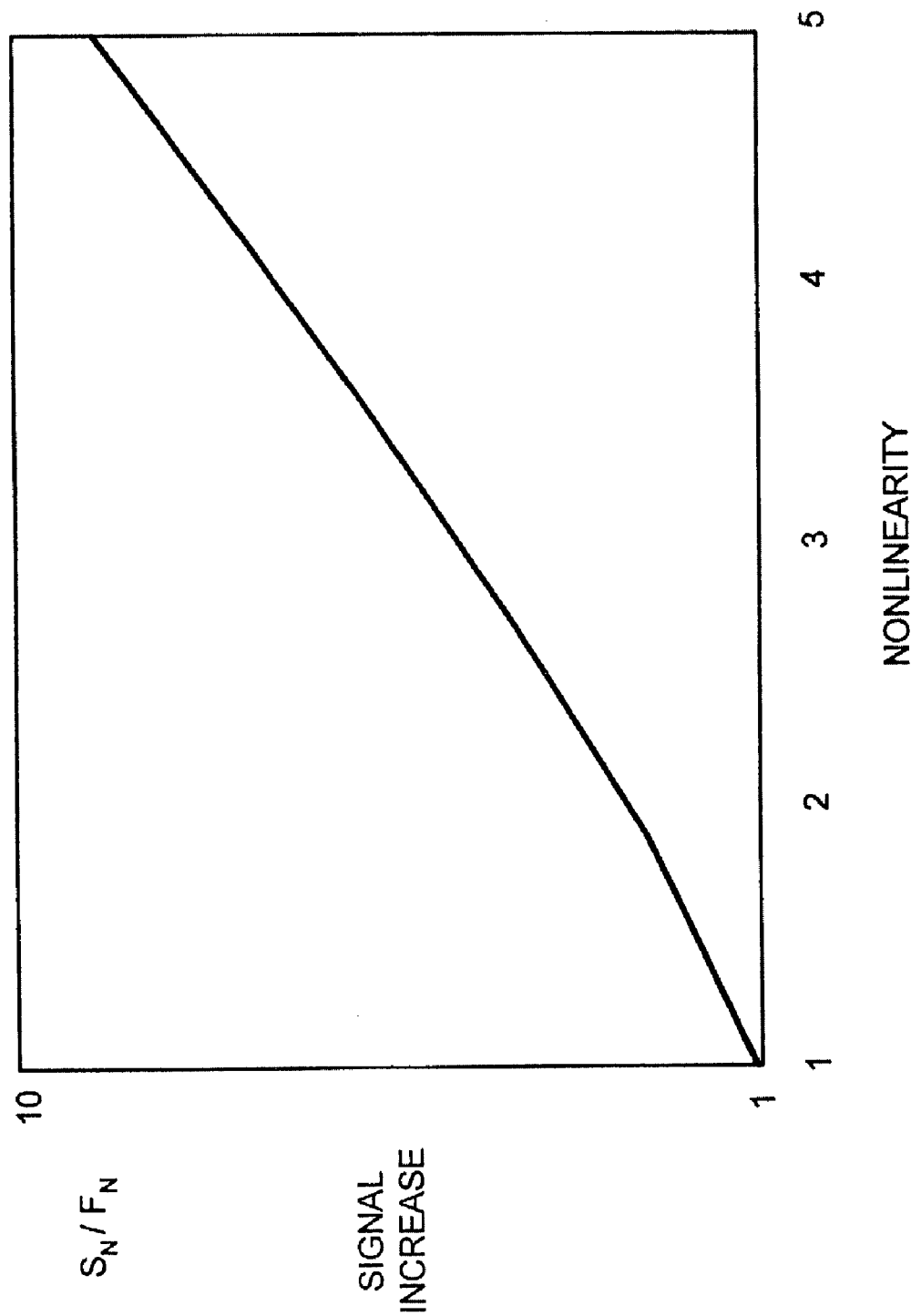
FIG. 21 graphically shows the specimen ion interaction using a structured scan line in comparison to a homogeneous scan line, the interocties being identical in both lines.

Once again, FIG. 21 shows generally the specimen interaction using a structured scan line in comparison to a homogeneous scan line, the intensities being identical in both lines. The ratio $S_N/F_N$ is shown as a function of the order of nonlinearity N. It will be seen that for N>1, i.e., for a nonlinear specimen interaction, the ratio is greater than 1. This means that at a constant average excitation intensity $I_0$ the efficiency of the specimen interaction increases through the use of a modulated line compared to a homogeneous scan line. In the case of a two-photon interaction, the efficiency is greater by a factor of 1.5, for example.

FIG. 22 shows schematically different constructions for generating two partial beams. The object beam paths are shown in each case. A distinction is made here between generating the partial beams by dividing the microscope pupil (FIGS. 22A and 22B.) and by using beam splitters (FIG. 22C), Splitting into two partial beams is carried out in a pupil plane of the microscope and in the xz plane of the microscope arrangement, i.e., in the plane in which the scan line is generated. A division of the pupil is particularly useful when a plurality of wavelengths are used over a wide spectral range, since the energy distribution on the two partial beams is not dependent upon wavelength. However, it is disadvantageous when the beam profile of the light source is not homogeneous. In this way, an unhomogeneous modulation depth along the scan line can be brought about in the arrangements A and B. This is prevented by the arrangement in FIG. 22C. However, requirements regarding the spectral characteristics of the beam splitter are stricter in this arrangement. In general, it is possible to adapt the beam profile, e.g., through the use of diffractive elements and a combination with arrangements according to FIGS. 22A, 22B or 22C.

Figure 22B:
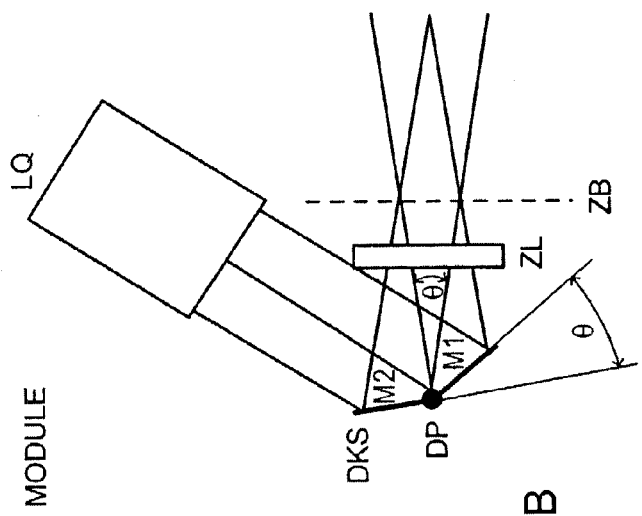
FIGS. 22A–D schematically show different constructions for generating two partial beams.
Figure 22D:
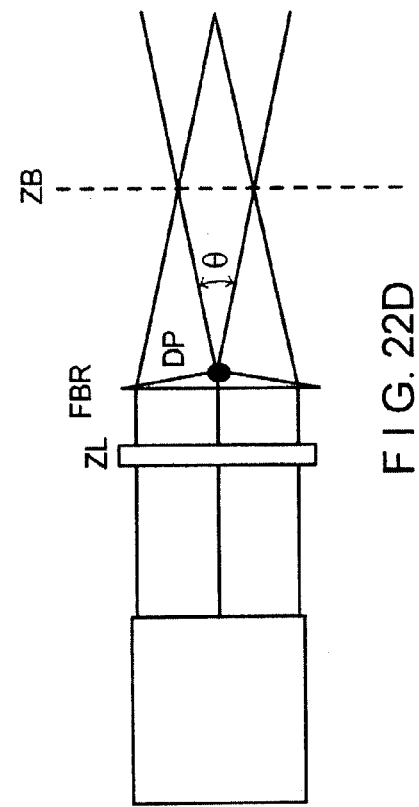
Figure 22A:
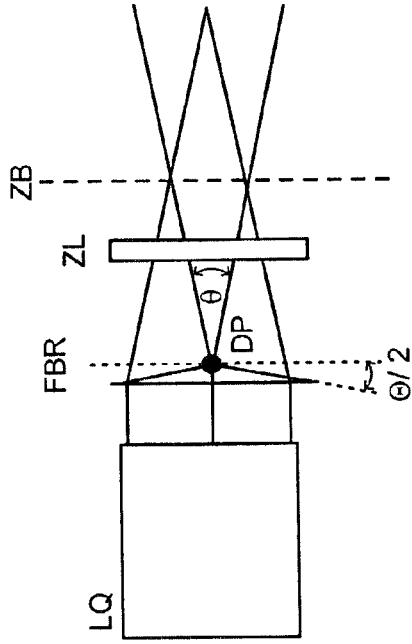

In FIG. 22A, light from the light source LQ which generates a collimated light bundle is transmitted through a Fresnel biprism FBP. The cylindrical lens ZL is located after FBP and acts in the plane vertical to the drawing plane and optical axis. As is shown in FIG. 22D, ZL can also be arranged in front of FBP without limitation. The splitting of the collimated beam of the light source into two partial beams of identical energy which enclose an angle θ of typically less than 5° is carried out by means of the biprism. The two partial beams intersect in an intermediate image ZB of the microscope arrangement. The line formed by the cylindrical optics ZL along the x-direction in the intermediate image is located in the xy plane. The drawing shows, by way of example, cylindrical optics ZL which focus the light of the light source LQ in the intermediate image ZB, i.e., the ZL stands at a distance exactly corresponding to the distance of focal length from the intermediate image. The partial beams reach the specimen through the following optics of the microscope arrangement (see FIGS. 9, 10, 11, 12 and 23) via the scanners X and Y, the scan optics SO, the tube lens TL and the objective O. In the specimen, the two partial beams overlap interferometrically and form a periodically structured scan line along the x-axis. The period of the scan line is dependent on the angle of inclination θ of the FBP (see FIG. 22A) and the wavelength of LQ. The image phase, i.e., $\varphi$can be deliberately adjusted by a rotation of FBP about the point of rotation DP in FIG. 22A. For a detailed description of the microscope arrangement and the method for generating the phase images and the calculation of the section images, reference is had to the preceding description. The advantage of variant A is that, by inserting FBP and ZL into the microscope beam path, a point-scanning laser scanning microscope can be reconfigured in a particularly advantageous manner to a microscope which scans in real time and in parallel manner. Further, the modulation frequency is highly dependent on the wavelength of the radiated light through the prismatic effect of FBP. This is advantageous especially for frequency coding (see above). However, the prismatic effect of FBP is problematic when using short pulse lasers with pulse lengths of less than 100 fs, since the individual spectral components of the laser pulses are imaged at different locations on the specimen and consequently can result in a widening of the pulses and therefore in a reduction in the pulse peak power. FIG. 22B therefore shows another advantageous arrangement. In this case, the splitting is carried out with a reflecting element such as a roof mirror DKS. DKS is arranged in the light source module (see FIGS. 9, 10, 11, 12 and 23) in such a way that the partial beams with identical energy intersect in ZB in the xz plane at an angle θ. ZL again focuses the LQ in the yz plane, so that a line is formed in ZB. By changing the angle between the two mirrors M1 and M2, e.g., by means of a piezo-actuator or a spindle pressing against M2 or M1, the angle θ between the two partial beams and, accordingly, the modulation frequency can be adjusted in a deliberate manner. In addition, an adjustment of the image phase $\varphi$can be carried out by a rotation of DKS about the axis of rotation DP shown in the drawing. The recording and calculation of the optical sections again take place in a manner analogous to the method already described above.

Figure 22C:
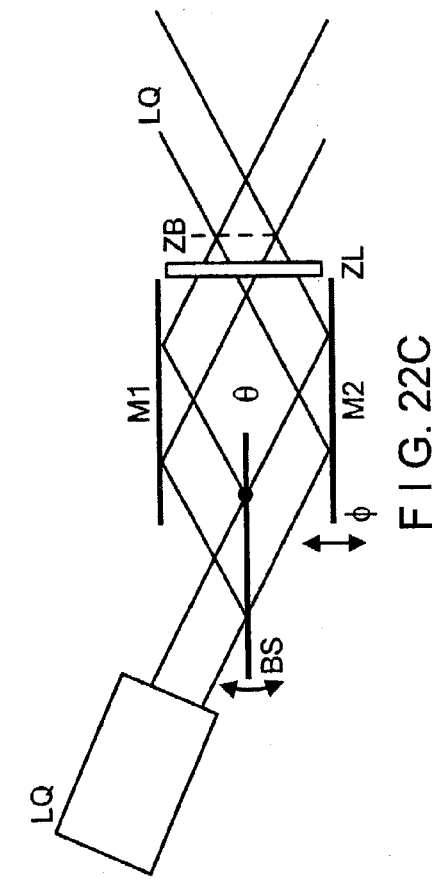

In the arrangement according to FIG. 22C, two partial beams with identical energy are generated through the beam splitter BS—a partially transmitting plane mirror. This was described, for example, in DE 19904592 A1. However, in this case, there is advantageously a cooperation with the element for shaping the line-shaped intensity distribution, e.g., by means of cylindrical lens ZL for generating a scan line.

The partial beams subsequently pass via two mirrors M1 and M2 in direction ZB so that they intersect exactly in ZB in the xz plane. ZL again focuses the beam in the yz plane so that a line is formed along x in ZB. The angle θ can be adjusted by the rotation of BS. The adjustment of the image phase $\varphi$can be carried out by a displacement of M1 or M2 or by jointly displacing M1 and M2 at a constant distance. The recording and calculation of the optical sections is again carried out in a manner analogous to the preceding description.

With regard to the complete arrangement of a microscope, particularly a laser scanning microscope, with the described arrangements for the interference of partial light beams, reference is had to the arrangements described above (e.g., FIGS. 9, 19, 23) which contain a light module.

While the foregoing description and drawings represent the present invention, it will be obvious to those skilled in the art that various changes may be made therein without departing from the true spirit and scope of the present invention.

The invention claimed is:

1. A method for depth-resolved optical detection of a specimen comprising the steps of:
   providing a scanning movement over the specimen or at least a part of the specimen of an illumination light distribution of at least one wavelength which is generated on or in the specimen;
   providing detection of the light which is influenced based on interaction with the specimen;
   said illumination light having a modulation in at least one spatial direction; and
   carrying out the scanning movement and detection associated with the scanning movement at least in a first and a second different phase position of the modulation and/or first and second frequency of the periodicity of the modulation; and
   calculating and presenting at least one optical section image through the specimen or through part of the specimen.

2. The method according to claim 1, wherein the modulation is carried out by impressing at least one structure which is spatially periodic in at least one dimension.

3. The method according to claim 1, wherein the light distribution is imaged on the specimen.

4. The method according to claim 1, wherein the section image is graphically displayed.

5. The method according to claim 1, wherein an optical imaging of a periodic structure is carried out.

6. The method according to claim 1, wherein at least one interference pattern is impressed on the specimen.

7. The method according to claim 1, wherein a plurality of frequencies and phase positions of the structure are imaged on the specimen simultaneously.

8. The method according to claim 1, wherein a plurality of frequencies and phase positions of the structure are imaged on the specimen sequentially.

9. The method according to claim 1, wherein the illumination is carried out by means of a line-shaped light distribution which has an extension of up to diffraction limitation in the narrow direction and, in the other direction at right angles thereto, a multiple of this extension.

10. The method according to claim 1, wherein pointwise scanning is carried out by means of the scanning movement.

11. The method according to claim 1, wherein a scanning movement of a line pattern and/or at least a one-dimensional or two-dimensional point pattern is carried out within a scan field.

12. The method according to claim 11, wherein a composite image is generated from the scanned line patterns and/or point patterns.

13. The method according to claim 11, wherein an equidistant raster of line patterns and/or point patterns is used.

14. The method according to claim 1, wherein the illumination light contains a plurality of wavelengths.

15. The method according to claim 1, wherein with n wavelengths at least n+1 phase positions of the structure are detected.

16. The method according to claim 1, wherein phase and/or frequency are adjusted differently for every wavelength for generating coding values.

17. The method according to claim 1, wherein a wavelength-dependent phase coding and/or frequency coding of the illumination light is carried out and the optical section image is calculated per wavelength by means of the coding.

18. The method according to claim 1, wherein the scan process is carried out with a line with a plurality of wavelengths.

19. The method according to claim 1, wherein the scan process is carried out with a plurality of lines simultaneously.

20. The method according to claim 19, wherein illumination is carried out with one or more wavelengths.

21. The method according to claim 1, wherein, in the calculation of phase images ($I_j(x)$) with image phase: $\phi_i$) with phase coding of the excitation wavelength ($\phi_j$), images are calculated which contain the image information of the pseudo-confocal section ($C_j$) and of background ($B_j$), which image information is characteristic of the respective jth wavelength:

$$I_0(x) = \sum_{j=1}^{n} C_j(x) \cdot \cos(k \cdot x + \phi_j + \varphi_0) + B_j(x)$$

$$I_1(x) = \sum_{j=1}^{n} C_j(x) \cdot \cos(k \cdot x + \phi_j + \varphi_1) + B_j(x)$$

$$I_2(x) = \sum_{j=1}^{n} C_j(x) \cdot \cos(k \cdot x + \phi_j + \varphi_2) + B_j(x)$$

...

$$I_n(x) = \sum_{j=1}^{n} C_j(x) \cdot \cos(k \cdot x + \phi_j + \varphi_n) + B_j(x)$$

wherein $$\begin{pmatrix} c_{11} & c_{12} & \cdots & \cdots \\ c_{21} & c_{22} & \cdots & \cdots \\ \cdots & \cdots & \cdots & \cdots \\ c_{n1} & c_{n2} & \cdots & c_{nm} \end{pmatrix} \cdot \begin{pmatrix} C_1 \\ C_2 \\ \cdots \\ C_n \end{pmatrix} = \begin{pmatrix} I_1 - I_0 \\ I_2 - I_0 \\ \cdots \\ I_n - I_0 \end{pmatrix},$$

where $c_{ij}(x) = \cos(k \cdot x \cdot \phi_j + \phi_i) - \cos(k \cdot x + \phi_j)$.

22. The method according to claim 1, using a periodic structure whose period changes at least in one spatial direction (Y) vertical to the direction of periodicity (X).

23. The method according to claim 1, using an optical arrangement with a dispersive unit which splits the illumination light into spectral components and joins it again and which has imaging optics for imaging the spectral components in a focal plane, wherein a periodic structure for influencing the illumination light in a wavelength-dependent manner is provided in or in the vicinity of the focal plane.

24. The method according to claim 1, wherein the generation of optical section images is carried out by structured illumination by means of recording individual images with different modulation frequency and/or image phase.

25. The method according to claim 1, wherein the optical section thickness is varied by changing the modulation frequency.

26. The method according to claim 1, wherein a phase coding is carried out with simultaneous imaging of different wavelengths and/or line foci on a common detector.

27. The method according to claim 1, wherein a frequency coding is carried out with simultaneous imaging of different wavelengths and/or line foci on a common detector.

28. The method according to claim 1, wherein a plurality of wavelengths are imaged simultaneously with respect to time on the specimen.

29. The method according to claim 28, wherein the imaging is carried out in a spatially separated manner or on a common location of the specimen.

30. The method according to claim 1, wherein a wavelength is imaged on the specimen.

31. The method according to claim 30, wherein the imaging is carried out in a repeatedly spatially separated manner or on a location of the specimen.

32. The method according to claim 1, wherein the light distribution is imaged on the specimen in a line-shaped or point-shaped manner.

33. The method according to claim 1, wherein a sequential recording of the individual images is carried out.

34. The method according to claim 1, wherein a plurality of line-shaped and/or point-shaped light distributions are generated.

35. The method according to claim 1, wherein a parallel recording of individual images is carried out.

36. The method according to claim 1, wherein, with a plurality of wavelengths, the section thicknesses are identically adjusted by changing the modulation frequency.

37. The method according to claim 1, wherein the detection is carried out with point detectors and/or line detectors and/or matrix detectors.

38. The method according to claim 1, wherein a wavelength-dependent phase coding is carried out by an arrangement for generating a wavelength-dependent parallel offset along the periodic structure.

39. The method according to claim 1, wherein a wavelength-dependent phase coding is carried out by a tilted plate in an intermediate image.

40. The method according to claim 1, wherein a wavelength-dependent phase coding is carried out by a dispersive element.

41. The method according to claim 1, wherein a wavelength-dependent phase coding is carried out by an optical arrangement with a dispersive unit which splits the illumination light into spectral components and unites them again, which optical arrangement has imaging optics for imaging the spectral components in a focal plane, wherein a periodic structure is provided in or in the vicinity of the focal plane for wavelength-dependent influencing of the illumination light, wherein the structure is rotatable about the optical axis.

42. The method according to claim 41, wherein the spectral splitting is carried out in an intermediate image.

43. The method according to claim 1, wherein a frequency coding of a plurality of wavelengths is carried out by an optical arrangement with a dispersive unit which splits the illumination light into spectral components and unites them again, which optical arrangement has imaging optics for imaging the spectral components in a focal plane, wherein a periodic structure is provided in or in the vicinity of the focal plane for wavelength-dependent influencing of the illumination light, with a periodic structure whose period changes at least in one spatial direction (Y) vertical to the direction of periodicity (X).

44. The method according to claim 1, wherein a frequency coding of a plurality of wavelengths is carried out in that the imaging scale is changed in a wavelength-dependent manner.

45. The method according to claim 1, wherein a frequency coding of a plurality of wavelengths is carried out by an optical arrangement with a dispersive unit which splits the illumination light into spectral components and unites them again, which optical arrangement has imaging optics for imaging the spectral components in a focal plane, wherein a periodic structure is provided in or in the vicinity of the focal plane for wavelength-dependent influencing of the illumination light, with a structure composed of a plurality of parts of different periodicity.

46. The method according to claim 1, wherein a sequential recording of the individual images is carried out with a change in the image phase.

47. The method according to claim 46, wherein a displacement of the periodic structure is carried out at right angles to the optical axis.

48. The method according to claim 1, wherein a sequential recording of the individual images is carried out with a change in the image phase by adjusting the position of the scanner.

49. The method according to claim 1, wherein a sequential recording of the individual images is carried out with a change in the image phase by tilting a plane-parallel plate.

50. The method according to claim 1, wherein a sequential recording of the individual images is carried out with a change in the modulation frequency.

51. The method according to claim 1, wherein a sequential recording of the individual images is carried out with a change in the modulation frequency by a wavelength-dependent change in the imaging scale.

52. The method according to claim 1, wherein a sequential recording of the individual images is carried out with a change in the modulation frequency by swiveling in different structures with different periodicity.

53. The method according to claim 1, wherein a sequential recording of the individual images is carried out with a change in the modulation frequency by a displacement of a periodic structure, whose period changes at least in one spatial direction (Y) essentially vertical to the direction of periodicity (X), vertical to the periodicity.

54. The method according to claim 1, wherein a plurality of light distributions are generated on the specimen and a parallel recording of the individual images is carried out.

55. The method according to claim 54, with generation of a plurality of light distributions on the specimen with a wavelength, by splitting the illumination into a plurality of partial beams with a beam splitter arrangement comprising at least one full mirror and a partially transmitting mirror or splitting the illumination into a plurality of partial beams with at least one mirror and a reflecting periodic structure acting as beam splitter.

56. The method according to claim 54, with generation of a plurality of light distributions on the specimen with a plurality of wavelengths, by splitting the illumination into a plurality of partial beams with a dispersive element or splitting the illumination into a plurality of partial beams by a beam splitter arrangement comprising at least one full mirror and a partially transmitting mirror or splitting the illumination into a plurality of partial beams with at least one mirror and a reflecting periodic structure acting as beam splitter.

57. The method according to claim 1, wherein a parallel recording of the individual images is carried out with different phase positions of the illumination.

58. The method according to claim 57, with a plurality of wavelengths, by means of an arrangement with a dispersive element and a periodic structure which is rotatable about the optical axis, wherein the dispersive element is preferably arranged in the intermediate image, and/or an arrangement with a dispersive element and a periodic structure comprising a plurality of parts of different periodicity and the dispersive element is preferably arranged in the intermediate image and/or arrangement with a dispersive element, wherein the periodic structure is reflecting and acts as a beam splitter.

59. The method according to claim 57, with one wavelength, by splitting the illumination into a plurality of partial beams with a beam splitter arrangement comprising at least one full mirror and a partially transmitting mirror or splitting the illumination into a plurality of partial beams with at least one mirror and a reflecting periodic structure acting as beam splitter, wherein the structure is rotatable about the optical axis, or by splitting the illumination into a plurality of partial beams with a beam splitter arrangement comprising at least one full mirror and a partially transmitting mirror or splitting the illumination into a plurality of partial beams with at least one mirror and a reflecting periodic structure acting as beam splitter, wherein the structure comprises a plurality of parts.

60. The method according to claim 1, wherein a parallel recording is carried out with different modulation frequency.

61. The method according to claim 60, with a plurality of wavelengths,
by means of arrangement of a dispersive element and a periodic structure whose period changes at least in one spatial direction (Y) essentially vertical to the direction of periodicity (X), or an arrangement with a dispersive element, wherein the periodic structure comprises parts of different periodicity, wherein the dispersive element is preferably arranged in an intermediate image.

62. The method according to claim 60, with one wavelength, by splitting the illumination into a plurality of partial beams with a beam splitter AO comprising at least one full mirror and a partially transmitting mirror or splitting the illumination into a plurality of partial beams with at least one mirror and a reflecting periodic structure, with a period structure whose period changes at least in one spatial direction (Y) essentially vertical to the direction of periodicity (X), or by splitting the illumination into a plurality of partial beams with a beam splitter AO comprising at least one full mirror and one partially transmitting mirror or by splitting the illumination into a plurality of partial beams with at least one mirror and a reflecting periodic structure, wherein the periodic structure comprises parts of different periodicity.

63. An arrangement for depth-resolved optical detection of a specimen, the light of an illumination light distribution which is influenced based on interaction with the specimen, comprising:
means for illuminating the specimen with at least one wavelength;
means for generating a relative movement between the specimen and illumination light;
means for imaging the light influenced by the specimen on at least one detector;
means for imaging a structure which changes in a spatially periodic manner in at least one dimension in different phases and/or frequencies of the periodicity on the specimen; and
means for calculating at least one optical section image from the local information of the light influenced by the specimen.

64. The arrangement according to claim 63, wherein means are provided for graphically displaying the section image.

65. The arrangement according to claim 63, wherein means are provided for imaging at least one interference pattern.

66. The arrangement according to claim 63, wherein the illumination is carried out by means of a line-shaped light distribution which has an extension of up to diffraction limitation in the narrow direction and, in the other direction at right angles thereto, a multiple of this extension.

67. The arrangement according to claim 63, wherein scanning is carried out in pointwise manner by means of the scanning movement.

68. The arrangement according to claim 63, wherein a scanning movement of a line pattern and/or at least a one-dimensional or two-dimensional point pattern is carried out within a scan field.

69. The arrangement according to claim 63, wherein a composite image is generated from a plurality of scanned line patterns and/or point patterns.

70. The arrangement according to claim 63, wherein an equidistant raster of line patterns and/or point patterns is used.

71. The arrangement according to claim 63, wherein the illumination light contains a plurality of wavelengths.

72. The arrangement according to claim 63, wherein the scan process is carried out with a line with a plurality of wavelengths.

73. The arrangement according to claim 63, wherein the scan process is carried out with a plurality of lines simultaneously.

74. The arrangement according to claim 63, wherein scanning is carried out with one or more wavelengths.

75. The arrangement according to claim 63, with a periodic structure whose period changes at least in one spatial direction (Y) vertical to the direction of periodicity (X).

76. The arrangement according to claim 63, with an optical arrangement with a dispersive unit which splits the illumination light into spectral components and unites them again and which has imaging optics for imaging the spectral components in a focal plane, wherein a periodic structure for influencing the illumination light in a wavelength-dependent manner is provided in or in the vicinity of the focal plane.

77. The arrangement according to claim 76, wherein the dispersive splitting is carried out in an intermediate image plane.

78. The arrangement according to claim 63, wherein a phase coding is carried out with simultaneous imaging of different wavelengths and/or line foci on a common detector.

79. The arrangement according to claim 63, wherein a frequency coding is carried out with simultaneous imaging of different wavelengths and/or line foci on a common detector.

80. The arrangement according to claim 63, wherein a plurality of wavelengths are imaged simultaneously with respect to time on the specimen.

81. The arrangement according to claim 63, wherein the imaging is carried out in a spatially separated manner or on a common location of the specimen.

82. The arrangement according to claim 63, wherein a wavelength is imaged on the specimen.

83. The arrangement according to claim 63, wherein the imaging is carried out in a repeatedly spatially separated manner or on a common location of the specimen.

84. The arrangement according to claim 63, wherein the light distribution is imaged on the specimen in a line-shaped or point-shaped manner.

85. The arrangement according to claim 63, wherein a sequential recording of the individual images is carried out.

86. The arrangement according to claim 63, wherein a plurality of line-shaped and/or point-shaped light distributions are provided.

87. The arrangement according to claim 63, wherein a parallel recording of individual images is carried out.

88. The arrangement according to claim 63, wherein the detection is carried out with point detectors and/or line detectors and/or matrix detectors.

89. The arrangement according to claim 63 for wavelength-dependent phase coding.

90. The arrangement according to claim 89, for generating a wavelength-dependent parallel offset along the periodic structure.

91. The arrangement according to claim 90, with a tilted plane-plate in an intermediate image.

92. The arrangement according to claim 90, with an element in an imaging pupil, which element is dispersive in the direction of periodicity.

* * * * *